(12) United States Patent
Blumenfeld et al.

(10) Patent No.: US 9,636,428 B2
(45) Date of Patent: May 2, 2017

(54) SULFONIC ESTERS OF METAL OXIDES AND METHODS OF THEIR USE

(71) Applicants: California Institute of Technology, Pasadena, CA (US); Children's Hospital Los Angeles, Los Angeles, CA (US)

(72) Inventors: Carl M. Blumenfeld, Pasadena, CA (US); Karn Sorasaenee, Altadena, CA (US); Harry B. Gray, Pasadena, CA (US); Robert H. Grubbs, South Pasadene, CA (US)

(73) Assignees: California Institute of Technology, Pasadena, CA (US); Children's Hospital of Los Angeles, Los Angeles, CA (US)

( * ) Notice: Subject to any disclaimer, the term of this patent is extended or adjusted under 35 U.S.C. 154(b) by 141 days.

(21) Appl. No.: 14/492,324

(22) Filed: Sep. 22, 2014

(65) Prior Publication Data

US 2015/0202331 A1 Jul. 23, 2015

Related U.S. Application Data

(63) Continuation of application No. 14/449,247, filed on Aug. 1, 2014, now abandoned.

(60) Provisional application No. 61/954,974, filed on Mar. 18, 2014, provisional application No. 61/928,762, filed on Jan. 17, 2014.

(51) Int. Cl.
    *A61B 5/055* (2006.01)
    *A61K 49/16* (2006.01)
    *A61K 49/10* (2006.01)
    *A61K 47/48* (2006.01)
    *A61K 49/00* (2006.01)

(52) U.S. Cl.
    CPC ........ *A61K 49/16* (2013.01); *A61K 47/48146* (2013.01); *A61K 49/0004* (2013.01); *A61K 49/0052* (2013.01); *A61K 49/0058* (2013.01); *A61K 49/106* (2013.01); *A61K 49/00* (2013.01)

(58) Field of Classification Search
    None
    See application file for complete search history.

(56) References Cited

U.S. PATENT DOCUMENTS

| 2,683,143 A | 7/1954 | White |
| 2006/0281087 A1 | 12/2006 | Sonezaki |
| 2010/0305335 A1 | 12/2010 | Palmer et al. |

OTHER PUBLICATIONS

Nilsson, et al., "Immobilization of Ligands with Organic Sulfonyl Chloride", Methods of Enzymology, 1984, vol. 104, 56-69.
Andersson, et al., Consecutive Microcontact Printing-Ligands for Asymmetric Catalysis in Silicon Channels, Apr. 2001, Sensors and Actuators B, vol. 79, 78-84.
Nelles, et al., Functionalization of Silicon Nanoparticles via Hydrosilylation with 1-Alkenes, Jan. 20, 2007, Colloid Polym. Sci., vol. 285, 729-736.
Accardo, et al., "Peptide-based Targeting Strategies for Simultaneous Imaging and Therapy with Nanovectors" Polymer J., May 2013, 45, 481-93.
Agadjanian et al, "Specific Delivery of Corroles to Cells via Noncovalent Conjugates with Viral Proteins", Pharmaceutical Research, Feb. 2006, 23(2), 367-377.
Aina, et al., "Therapeutic Cancer Targeting Peptides", Biopolymers, Oct. 2002, 66(3), 184-99.
Allen, "Ligand-Targeted Therapeutics in Anticancer Therapy", Nature Rev. Cancer, Oct. 2, 2002, 2(10), 750-63.
Almadhoun et al, "Nanocomposites of Ferroelectric Polymers With Surface-Hydroxylated BaTiO3 Nanoparticles for Energy Storage Applications", Chem., May 2012, 22, 11196.
Arkles, "Silane Coupling Agents Connecting Across Boundaries", 2006, Version 2.0, 60 pages.
Autret et al, "Synthesis and Electrochemistry of Iron( 111) Corroles Containing a Nitrosyl Axial Ligand. Spectral Characterization of [(OEC)FeT1l(NO)]nW here n=0, 1, 2, or -1 and OEC is the Trianion of 2,3,7,8,12,13,17,18-Octaethylcorrol", J. Am. Chem. Soc., 1994,116, 9141-9149.
Aviv et al, "Corrole-Based Applications", Chemical Communications, May 28, 2007, 1987-1999.
Barata et al., "Corrole-Silica Hybrid Particles: Synthesis and Effects on Singlet Oxygen Generation", RSC Adv., Oct. 24, 2012, 3, 274-80.
Barbe et al, "Metallocorroles As Sensing Components for Gas Sensors: Remarkable Affinity and Selectivity of Cobalt(III) Corroles for CO vs. O2 and N2", The Royal Society of Chemistry, Mar. 23, 2004, 1208-1214.

(Continued)

*Primary Examiner* — Michael G Hartley
*Assistant Examiner* — Melissa Perreira
(74) *Attorney, Agent, or Firm* — Baker & Hostetler LLP

(57) ABSTRACT

The present disclosure is directed to sulfonic esters of metal oxides including those of formulas I and II:

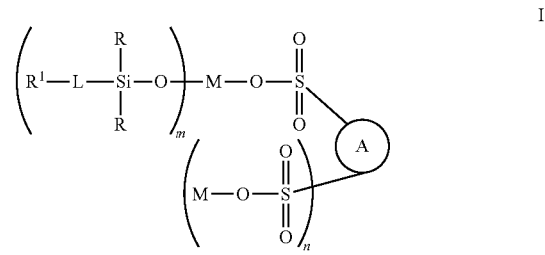

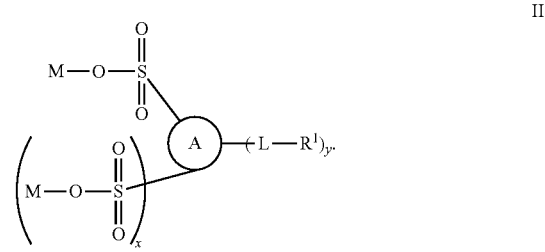

52 Claims, 10 Drawing Sheets

(56) References Cited

OTHER PUBLICATIONS

Blumenfeld et al, "Decorating Metal Oxide Surfaces with Fluorescent Chlorosulfonated Corroles", Inorganic Chemistry, Apr. 2013, 52, 4774-4776.
Haber et al, "Protecting the Beneficial Functionality of Lipoproteins by 1-fe, A Corrole-Based Catalytic Antioxidant", Chem. Sci., 2011, 2, 295-302.
Hori, T. and Osuka, A., "Nucleophilic Substitution Reactions of meso-5,10,15-Tris(pentafluorophenyl)-corrole; Synthesis of ABC-Type Corroles and Corrole-Based Organogels", Eur. J. Org. Chem., 2010, 2379-2386.
Hwang et al, "Photoexcitation of Tumor-Targeted Corroles Induces Singlet Oxygen-Mediated Augmentation of Cytotoxicity", Journal of Controlled Release, 2012, 163, 368-373.
Ikeda, et al., "Lateral Distribution of N3 Dye Molecules on TiO2 (110) Surface", Journal of Photochemistry, 2009, 202, pp. 185-190.
Jaracz, et al., "Recent Advances in Tumor-Targeting Anticancer Drug Conjugates" Bioorg. Med. Chem., Dec. 2005, 13(17), 5043-54.
Jin, et al., "Targeted Delivery System of Nanobiomaterials in Anticancer Therapy from Cells to Clinics", BioMed. Res. Inti., Feb. 2014, 24 pages.
Kanamori et al, "Neuroprotection Against Superoxide Anion Radical by Metallocorroles in Cellular and Murine Models of Optic Neuropathy", Journal of Neurochemistry, 2010, 114, 488-498.
Mahammed et al, "Highly Selective Chlorosulfonation of Tris(Pentafluorophenyl)Corrole as a Synthetic Tool for the Preparation of Amphiphilic Corroles and Metal Complexes of Planar Chirality", Organic Letters, Nov. 1, 2001, 3(22), 3443-3436.
Okun et al, "Manganese Corroles Prevent Intracellular Nitration and Subsequent Death of Insulin-Producing Cells", ACS Chemical Biology, 4(11), 910-914, 2009.
Palmer, J., "Transition Metal Corrole Coordination Chemistry", Struct Bond, 2012, 142: 49-90, Published online: Sep. 14, 2011.
Saltsman et al, "Selective Substitution of Corroles: Nitration, Hydroformylation, and Chlorosulfonation", J. Am. Chem. Soc. Jun. 26, 2002, 124(25):7411-20.
Sapsford, et al., "Functionalizing Nanoparticles with Biological Molecules:Developing Chemistires that Facilitate Nanotechnology", American Chemical Society, Feb. 22, 2013, pp. 1904-2074.
Simkhovich et al, "Mono- and Binuclear Ruthenium Corroles: Synthesis, Spectroscopy, Electrochemistry, and Structural Characterization", Chem. Eur. J. 2003, 9(1), 201-208.
Simkhovich et al, "Synthesis and Characterization of Germanium, Tin, Phosphorus, Iron, and Rhodium Complexes of Tris(pentafluorophenyl)corrole, and the Utilization of the Iron and Rhodium Corroles as Cyclopropanation Catalysts", Chem. Eur. J., 2001, 7(5), 1041-1055.
Tamura, et al, "Mechanism of Hydroxylation of Metal Oxide Surfaces", Journal of Colloid and Interface Sci., Nov. 2001, 243(1), 202-207.
Tortora et al, "Supramolecular Sensing Mechanism of Corrole Thin Films", Sensors and Actuartors B, 2013, 187, 72-77.
Viskota, et al., "Surface Functionalization of Barium Titanate SHG Nanoprobes for In Vivo Imaging in Zebrafish", Protocol, vol. 7(9), Aug. 9, 2012, pp. 1618-1633.
Wang, et al., "Characteristics of High Efficiency Dye-Sensitized Solar Cells", J. Phys. Chem., Jul. 6, 2006, 110(50), pp. 25210-25221.
Weaver "Corroles", May 5, 2005, 132 pages.

(a)  (b)

SULFONIC ESTERS OF METAL OXIDES AND METHODS OF THEIR USE

CROSS REFERENCE TO RELATED APPLICATIONS

This application is a continuation of U.S. application Ser. No. 14/449,247, filed Aug. 1, 2014, which claims the benefit of U.S. Provisional Application Nos. 61/954,974, filed Mar. 18, 2014 and 61/928,762, filed Jan. 17, 2014, the entireties of which are incorporated by reference herein.

TECHNICAL FIELD

The present disclosure is directed to multi-functionalized sulfonic esters of metal oxides and their uses.

BACKGROUND

Corroles are tetrapyrrolic macrocycles:

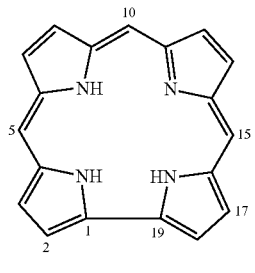

Corrole

Corroles are becoming increasing useful in the field of chemical synthesis as catalysts in, for example, oxidation, hydroxylation, hydroperoxidation, epoxidation, sulfoxidation, reduction, and group transfer reactions. See, e.g., Aviv, I., Gross, Z., Chem. Commun., 2007, 1987-1999. Based on their physico-chemical properties, it is envisioned that corroles could be useful in the sensors field and biomedical field. Id. Corrole-based materials useful in the chemical synthesis, sensor, biomedical, and other fields are needed.

SUMMARY

The present disclosure is directed to materials of formula I:

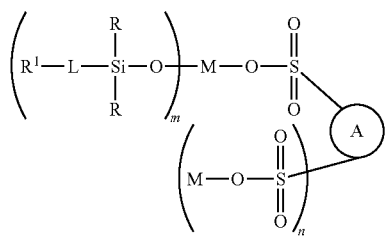

wherein A is a corrolyl or metallated corrolyl;
M is a surface comprising $TiO_2$, $BaTiO_3$, $SnO_2$, $Al_2O_3$, $Fe_2O_3$, $Fe_3O_4$, $ZrO_2$, $CeO_2$, CdO, $Cr_2O_3$, CuO, MnO, $Mn_2O_3$, $MnO_2$, NiO, SnO, $SnO_2$, $SiO_2$, or ZnO;
each R is independently $C_{1-6}$alkyl;
L is a linker;
each $R^1$ is a non-antibody moiety or an antibody moiety, wherein the non-antibody moiety or the antibody moiety is optionally complexed to a target;
m is 1, 2, 3, or 4; and
n is 0 or 1.

The present disclosure is also directed to materials of formula II:

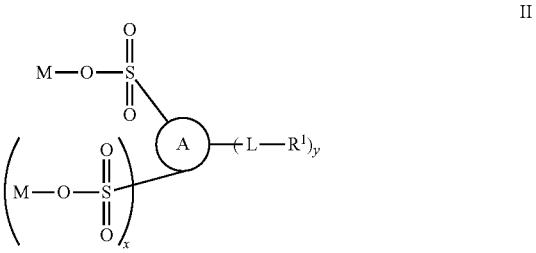

wherein A is a corrolyl or metallated corrolyl;
M is a surface comprising $TiO_2$, $BaTiO_3$, $SnO_2$, $Al_2O_3$, $Fe_2O_3$, $Fe_3O_4$, $ZrO_2$, $CeO_2$, CdO, $Cr_2O_3$, CuO, MnO, $Mn_2O_3$, $MnO_2$, NiO, SnO, $SnO_2$, $SiO_2$, or ZnO;
L is a linker;
$R^1$ is a non-antibody moiety or an antibody moiety, wherein the non-antibody moiety or the antibody moiety is optionally complexed to a target;
y is 1, 2, or 3; and
x is 0 or 1.

Methods of making materials of formulas I and II are described herein. Also described are methods of using the materials of the disclosure in applications such as optical imaging.

DETAILED DESCRIPTION OF ILLUSTRATIVE EMBODIMENTS

Figure 1:
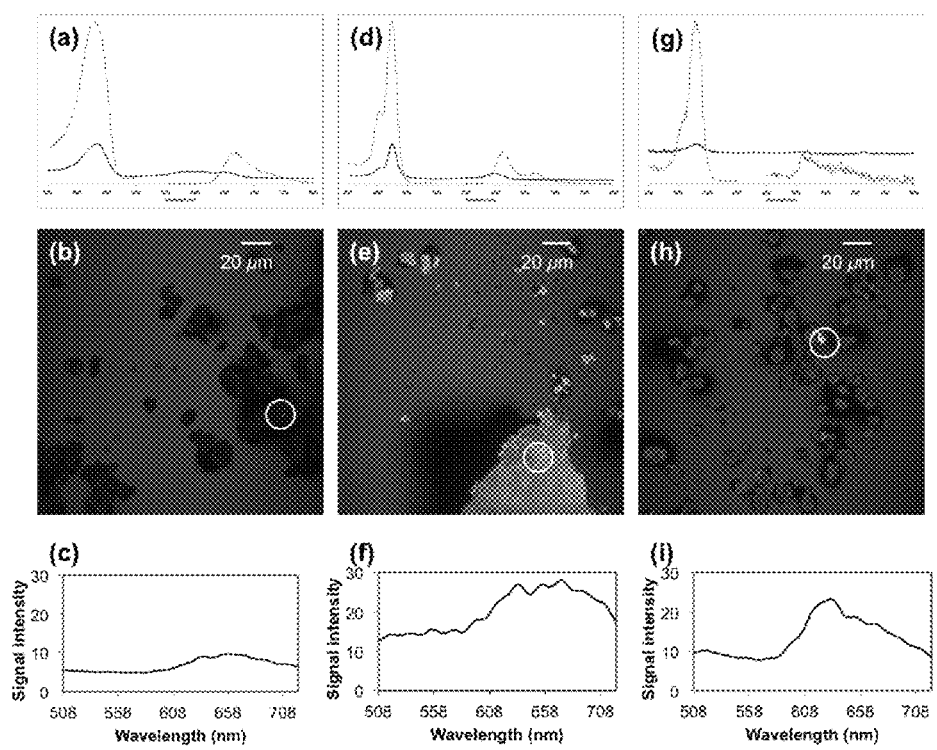
FIG. 1 depicts confocal fluorescence microscopy images of $1\text{-}TiO_2$ [(a), (b), (c)], $1\text{-}Al\text{-}TiO_2$ [(d), (e), (f)], and $1\text{-}Ga\text{-}TiO_2$ [(d), (e), (f)].

The present disclosure is directed to multi-functionalized materials, preferably nanoparticulate materials, comprising a metal oxide covalently bonded to a corrolyl or metallated-corrolyl through an —SO$_2$— linkage. The metal oxides for use in making the materials of the disclosure include those having at least one —OH group. Such metal oxides are known in the art and are described in further detail below.

One embodiment of the disclosure is directed to materials according to formula I:

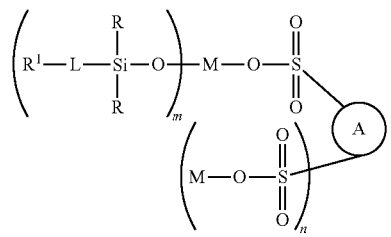

I wherein A is a corrolyl or metallated corrolyl;
M is a surface comprising TiO$_2$, BaTiO$_3$, SnO$_2$, Al$_2$O$_3$, Fe$_2$O$_3$, Fe$_3$O$_4$, ZrO$_2$, CeO$_2$, CdO, Cr$_2$O$_3$, CuO, MnO, Mn$_2$O$_3$, MnO$_2$, NiO, SnO, SnO$_2$, SiO$_2$, or ZnO;
each R is independently C$_{1-6}$alkyl;
L is a linker;
each R$^1$ is a non-antibody moiety or an antibody moiety, wherein the non-antibody moiety or the antibody moiety is optionally complexed to a target;
m is 1, 2, 3, or 4; and
n is 0 or 1.

Within the scope of the disclosure, M is a surface that comprises a metal oxide, for example, a metal oxide that comprises at least one —OH group. The —OH group can be inherently present on the surface. Alternatively, the at least one —OH group can be incorporated by oxidizing the surface with a reagent such as hydrogen peroxide. Preferred surfaces for use in the disclosure include metal oxides such as TiO$_2$, BaTiO$_3$, SnO$_2$, Al$_2$O$_3$, Fe$_2$O$_3$, Fe$_3$O$_4$, ZrO$_2$, CeO$_2$, CdO, Cr$_2$O$_3$, CuO, MnO, Mn$_2$O$_3$, MnO$_2$, NiO, SnO, SnO$_2$, SiO$_2$, and ZnO. In some embodiments, the surface comprises TiO$_2$. In some embodiments, the surface comprises BaTiO$_3$. In some embodiments, the surface comprises SnO$_2$. In some embodiments, the surface comprises Al$_2$O$_3$. In some embodiments, the surface comprises Fe$_2$O$_3$. In some embodiments, the surface comprises Fe$_3$O$_4$. In some embodiments, the surface comprises ZrO$_2$. In some embodiments, the surface comprises CeO$_2$. In some embodiments, the surface comprises CdO. In some embodiments, the surface comprises Cr$_2$O$_3$. In some embodiments, the surface comprises CuO. In some embodiments, the surface comprises MnO. In some embodiments, the surface comprises Mn$_2$O$_3$. In some embodiments, the surface comprises MnO$_2$. In some embodiments, the surface comprises NiO. In some embodiments, the surface comprises SnO. In some embodiments, the surface comprises SnO$_2$. In some embodiments, the surface comprises SiO$_2$. In some embodiments, the surface comprises ZnO.

In preferred embodiments, the surface is a nanoparticle surface. In other preferred methods of the disclosure, the surface comprises TiO$_2$.

Corroles for use in the disclosure are known in the art and are of the general formula:

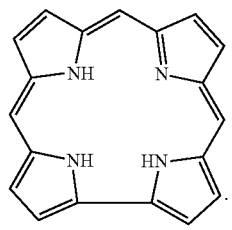

The corroles of the disclosure described herein can be attached to the M-OSO$_2$-moiety(ies) of the disclosure through any available carbon. Preferred corrolyls for use in the disclosure are 2,17-substituted corrolyls:

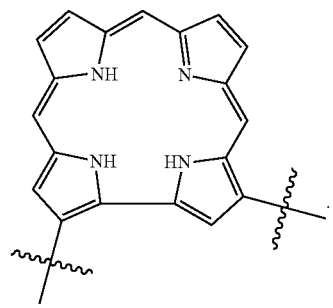 [SMILES: *c1cc2[nH]c1cc1nc(cc3ccc(cc4cc(*)c2[nH]4)[nH]3)C=C1]

Particularly preferred corroles for use in the disclosure include those of the following general formula:

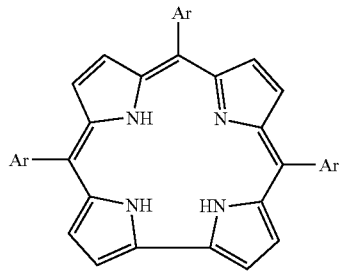

wherein Ar is an aryl group, for example, a phenyl or naphthyl group. In some embodiments of the disclosure, the aryl group is unsubstituted. In other embodiments, the aryl group is substituted. For example, when the aryl group is phenyl, the phenyl can be optionally substituted with halogen, for example, 1 to 5 halogen, that is, one or more of F, Cl, Br, or I, with F being a particularly preferred halogen. In exemplary embodiments, the aryl group is pentafluorophenyl. In other embodiments, when the aryl group is naphthyl, the naphthyl can be optionally substituted with 1 to 7 halogen, with F being a particularly preferred halogen. In preferred embodiments, the corrolyl is a 2,17-substituted corrolyl:

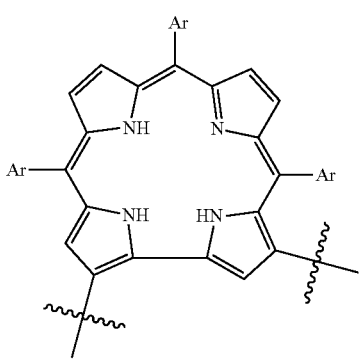

Preferred corrolyls for use in the disclosure are those wherein Ar is pentafluorophenyl and include

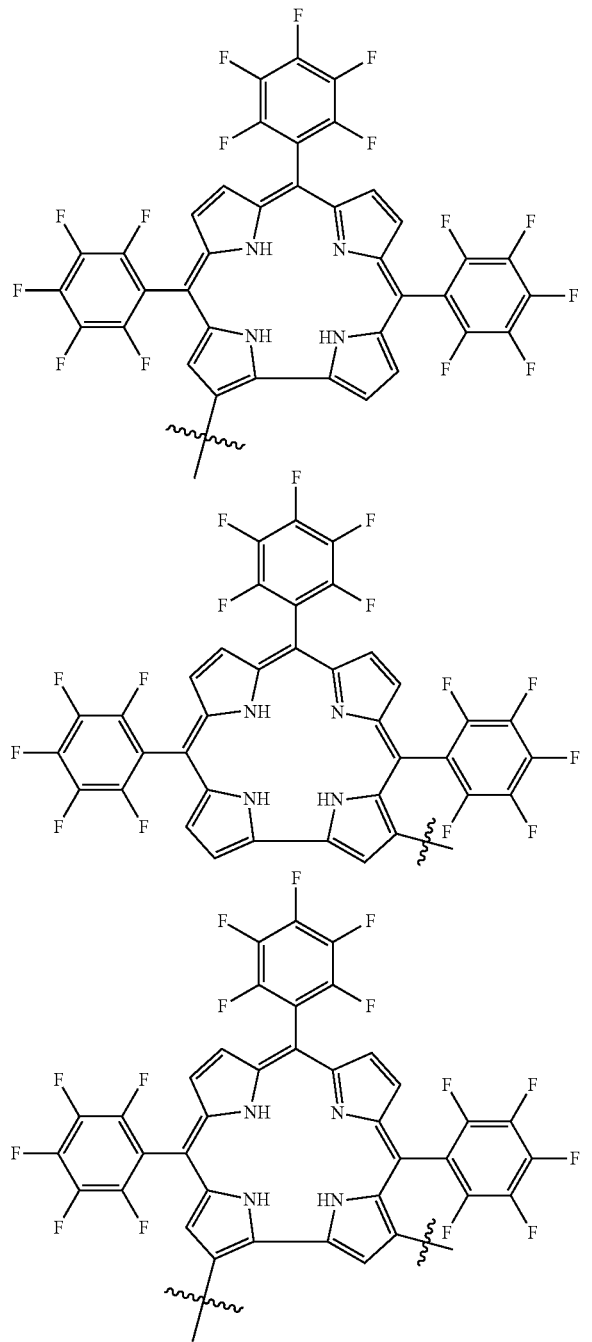

In addition to being substituted with one or more halogens, the aryl group can be further substituted with —NR$^3$R$^4$, wherein R$^3$ and R$^4$ are each independently H, C$_{1-10}$alkyl, C$_{1-10}$alkenyl, or -alkaryl; or R$^3$ and R$^4$, together with the nitrogen atom to which they are attached, form a heterocycloalkyl ring, which may be optionally subsituted with C$_{1-6}$alkyl, for example, methyl or ethyl. Examples of —NR$^3$R$^4$ moieties include:

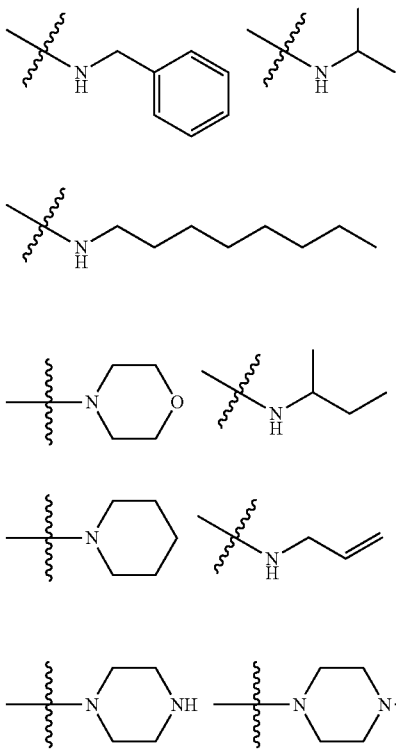

Corroles incorporating an —NR$^3$R$^4$ substituted aryl group can be accessed using methods known in the art, for example, using nucleophic substitution reactions. See, e.g., Hori, T., Osuka, A. Eur. J. Org. Chem. 2010, 2379-2386. For example, corroles incorporating an —NR$^3$R$^4$ substituted aryl group can be accessed using the following synthetic scheme:

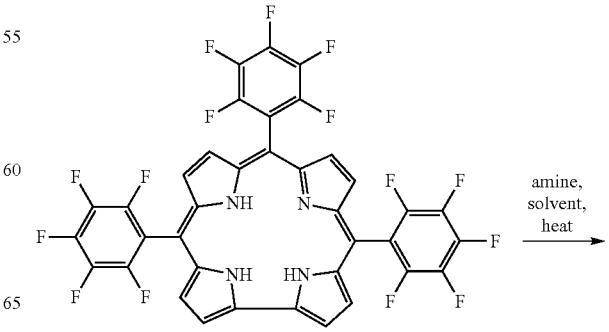

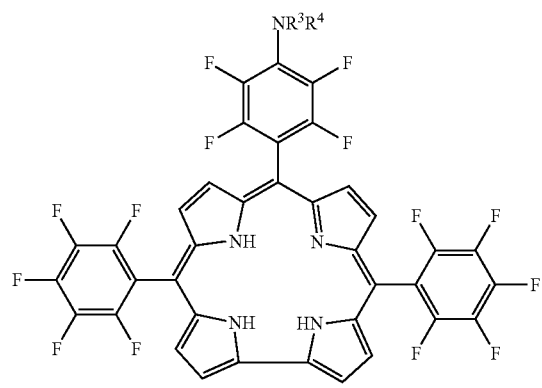

+

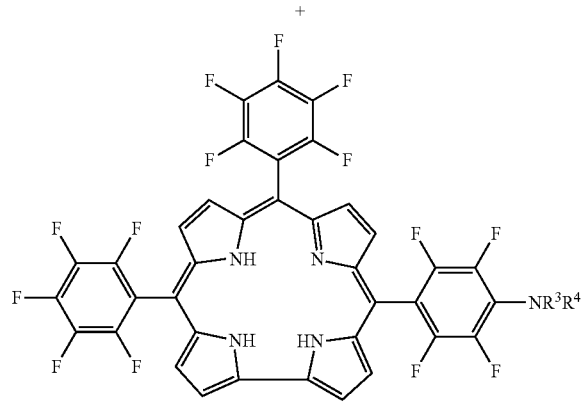

Amines that can be used in nucleophilic substitution reactions include, for example, benzylamine, octylamine, sec-butylamine, allylamine, dimethylamine, morphiline, piperidine, and N-methylpiperazine.

Another preferred corrole for use in the disclosure is of the general formula

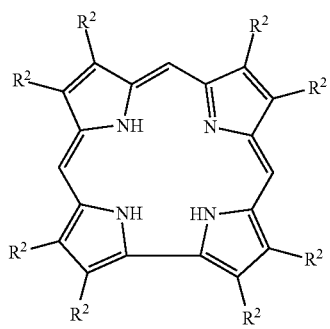

wherein each $R^2$ is independently H, $C_{1-6}$alkyl, halogen, or M-O—$SO_2$—, wherein M is as described above. Preferably, the corrolyl is a 2,17-substituted corrolyl:

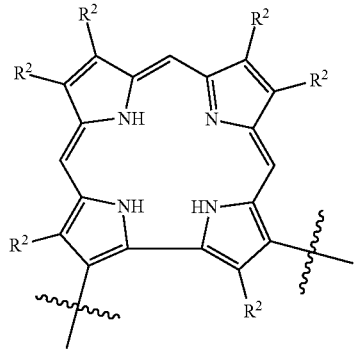

Yet another preferred corrole for use in the disclosure is of the general formula

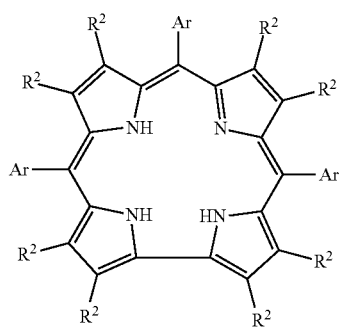

wherein Ar and $R^2$ are as previously described. Preferably, the corrolyl is a 2,17-substituted corrolyl:

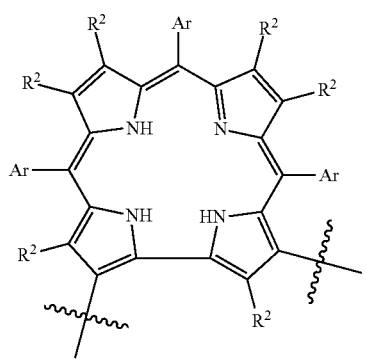

Corroles for use in the disclosure can also be metallated. In metallating a corrole, the nitrogens of the corrole are coordinated to a metal. Metals for use in the metallated corroles of the disclosure include any metal known in the art to be useful for coordinating to a corrole. Those of skill in the art understand that the function and use of the corrole can be modified by changing the coordinated metal.

For example, metals for use in metallating the corroles of the disclosure include Al, Ga, Fe, Mn, Sb, Co, Cr, Rh, Ru, Ro, Ir, V, Re, Cu, Sn, Ge, Ti, and Mo. Particularly preferred metals include Al and Ga. Another preferred metal is Fe. Yet another preferred metal is Mn. Another metal for use in the disclosure is Sb. Another metal for use in the disclosure is Co. Another metal for use in the disclosure is Cr. Another metal for use in the disclosure is Rh. Another metal for use in the disclosure is Ru. Another metal for use in the disclosure is Ro. Another metal for use in the disclosure is Ir. Another metal for use in the disclosure is V. Another metal for use in the disclosure is Re. Another metal for use in the disclosure is Cu. Another metal for use in the disclosure is Sn. Another metal for use in the disclosure is Ge. Another metal for use in the disclosure is Ti. Another metal for use in the disclosure is Mo.

The metals for use in metallating the corroles of the disclosure can be optionally coordinated to one or more ligands. Such ligands are known in the art and include, for example, pyridine, nitrosyl, imido, nitrido, oxo, ether, hydroxyl, chloride, carbonyl, fluoro, bromo, phenyl, iodo, phosphine, arsine, and the like. Those skilled in the art would readily be able to determine a suitable ligand for any particular metal. A particularly preferred ligand for use in the disclosure is pyridine. Preferred metal-ligand moieties include Al(ligand)$_2$ and Ga(ligand), with Al(pyridine)$_2$ and Ga(pyridine) being particularly preferred.

While 2,17 substituted corroles have been particularly set forth herein, these examples are exemplary only and are not meant to limit the disclosure. It is envisioned that substitution at any position of the corrolyl or metallated corrolyl is within the scope of the disclosure.

Compounds of the disclosure can be prepared according to methods known in the art. See, e.g., (a) Mahammed, A.; Goldberg, I.; Gross, Z. *Org. Lett.* 2001, 3, 3443. (b) Saltsman, I.; Mahammed, A.; Goldberg, I.; Tkachecko, E.; Botoshansky, M.; Gross, Z. *J. Am. Chem. Soc.* 2002, 124, 7411. See also, Blumenfeld, C. M.; Grubbs, R. H.; Moats, R. A.; Gray, H. B.; Sorasaenee, K. *Inorg. Chem.* 2013, 52, 4774. One exemplary method of preparing compounds of the disclosure are shown in Scheme 1.

Scheme 1

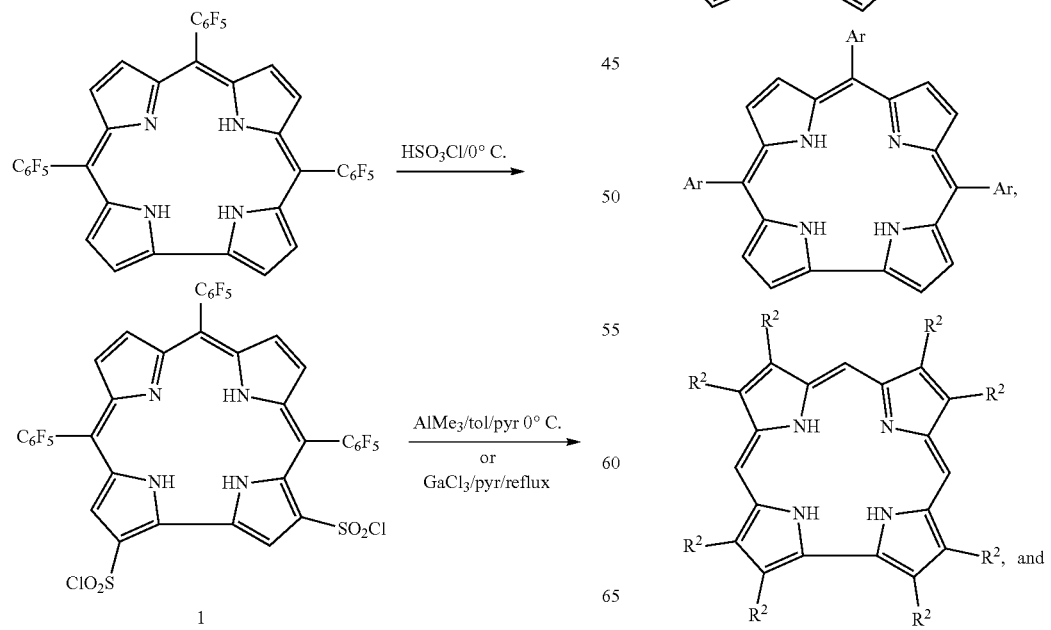

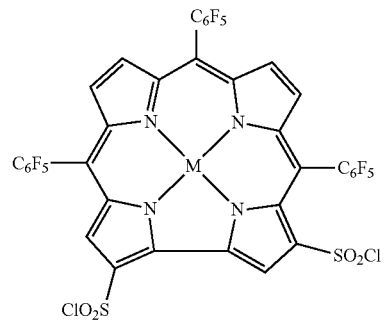

M = Al(py$_2$) (1-Al) or Ga(py) (1-Ga)
py = pyridine

The corrole or metallated corrole used in any of the methods of preparing materials of formula I can be any of the corroles or metallated corroles described herein.

Corrole coupling to the metal oxide surfaces of the disclosure can be performed by mixing metals of the disclosure bearing hydroxylated surfaces, preferably in nanocrystal form, with solutions of corrole and heating, preferably to reflux. After repeated washing with copious amounts of solvent such as, for example, CH$_2$Cl$_2$, acetone, and water, and drying under vacuum, powders are obtained.

Preferred corroles for use in the methods of making materials of formula I include:

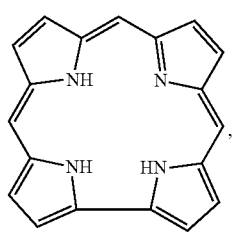

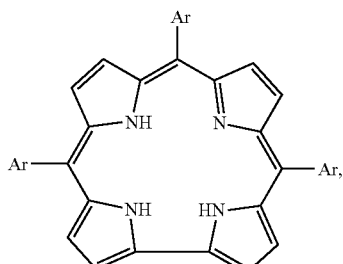

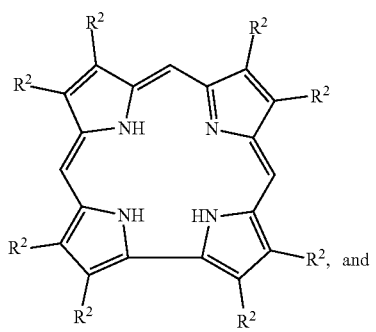

11
-continued
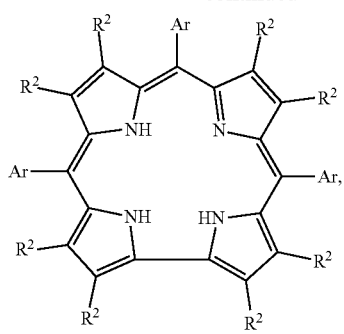
wherein Ar and $R^2$ are as set forth above.
Preferably, the corrolyls are 2,17-substituted corrolyls:
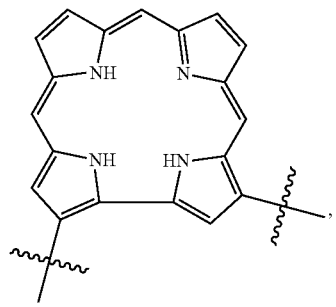
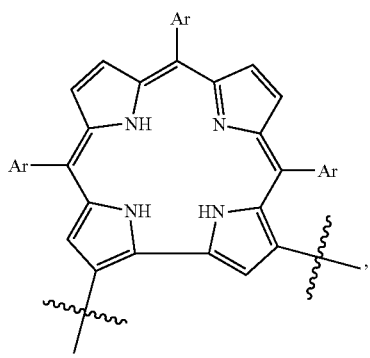
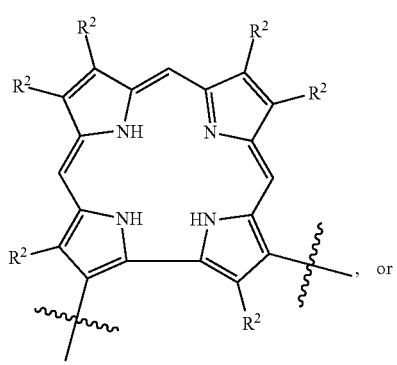, or
12
-continued
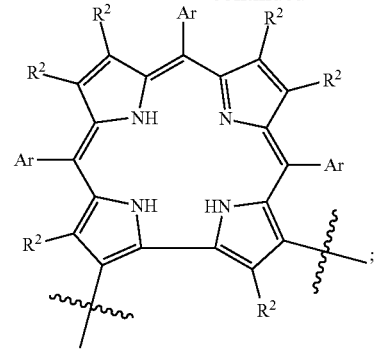
wherein Ar and $R^2$ are as set forth above.
Preferred metallated corroles for use in the methods of the disclosure include:
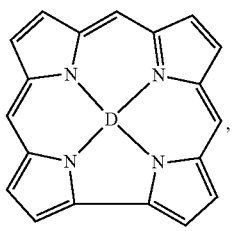
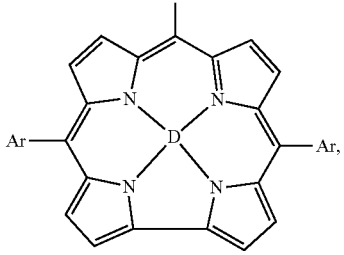
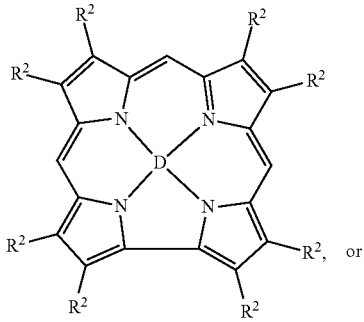, or
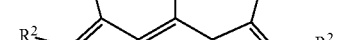
wherein Ar and $R^2$ are as set forth herein above and wherein D is Al, Ga, Fe, Mn, Sb, Co, Cr, Rh, Ru, Ro, Ir, V, Re, Cu, Sn, Ge, Ti, or Mo, each of which is optionally coordinated to one or more ligands. In some embodiments, D is D is Al(ligand)$_2$ or Ga(ligand). In preferred embodiments, the ligand is pyridine.

Preferably, the metallated corrolyls are 2,17-substituted corrolyls:

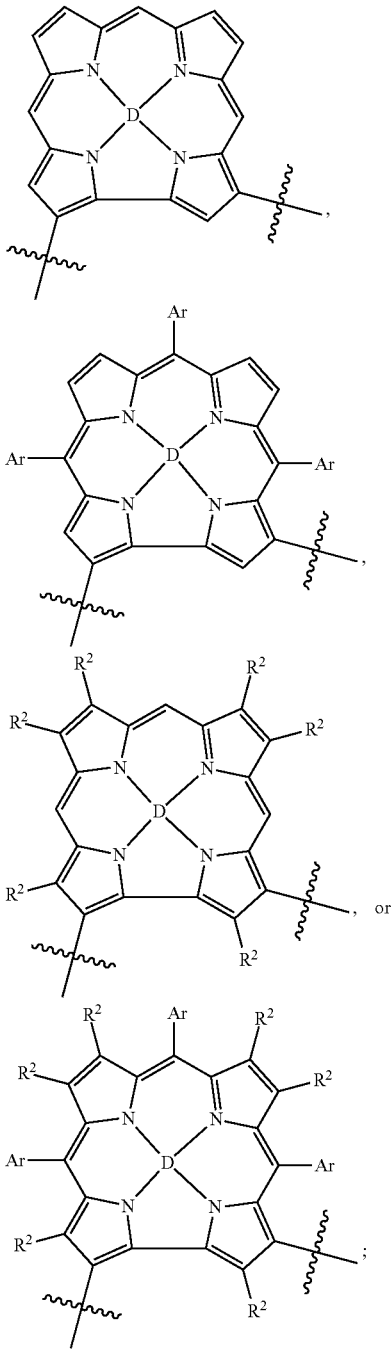

wherein Ar, R$^2$, and D are as set forth above.

In preferred embodiments of the disclosure, n is 0. In other embodiments, n is 1.

In other embodiments of the disclosure, m is at least 1. In other embodiments, m is 2. In yet other embodiments, m is 3. In still other embodiments, m is 4.

Within the scope of the disclosure, L is a linker moiety. Any suitable linker silyl linker can be used within the scope of the disclosure. Examples of linkers include, for example:

—(CH$_2$)$_{1-20}$—C=N—

—(CH$_2$)$_{1-20}$—NH— phenylen—NH—

—(CH$_2$)$_{1-20}$—C(O)—O—

—(CH$_2$)$_{1-20}$—

—(CH$_2$)$_{1-20}$—NH—C(O)—O—

—(CH$_{21-20}$)—SH—

A preferred L moiety is

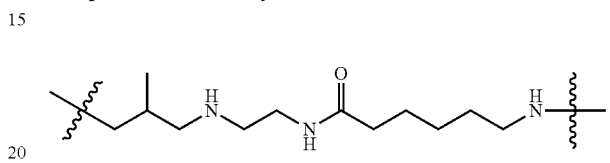

Those skilled in the art will appreciate that commercial sources of linker precursor reagents are available. See, e.g., Gelest, Inc. Morrisville, Pa. Examples of silyl reagents, and their coupling partners, that can be used within the scope of the disclosure are depicted in Table 1.

TABLE 1

| Silyl reagent | Coupling Partner |
| --- | --- |
| Aldehyde functional group | |
| (C$_2$H$_5$O)$_3$Si(CH$_2$)$_{10}$CHO<br>(C$_2$H$_5$O)$_3$Si(CH$_2$)$_3$CHO | Aminooxies, Hydrazides |
| Amino functional group | |
| (C$_2$H$_5$O)$_3$Si(CH$_2$)$_3$NH$_2$<br>(CH$_3$O)$_3$SiC$_6$H$_4$NH$_2$<br>(CH$_3$O)$_3$Si(CH$_2$)$_2$C$_5$H$_4$N<br>(CH$_3$O)$_3$Si(CH$_2$)$_3$NH(C$_4$H$_9$)<br>(CH$_3$O)$_2$(CH$_3$)SiCH$_2$NHC$_6$H$_5$<br>(CH$_3$O)$_2$Si(CH$_2$CH(CH$_3$)CH$_2$N(CH$_3$)) | Carboxylates, Halides (nucleophilic substitution) |
| Azide functional group | |
| (C$_2$H$_5$O)$_3$Si(CH$_2$)$_6$SO$_2$N$_3$ | Alkynes, Triaryl phosphines |
| Carboxylate functional group | |
| (OH)$_3$Si(CH$_2$)$_2$COOH | Amines, Alcohols |
| Sulfonate functional group | |
| (OH)$_3$Si(CH$_2$)$_3$SO$_3$H | Amines, Alcohols |
| Ester functional group | |
| (C$_2$H$_5$O)$_3$SiCH$_2$CO$_2$CH$_3$<br>(CH$_3$O)$_3$Si(CH$_2$)$_3$CO$_2$C$_6$H$_5$ | Amines |
| Halogen functional group | |
| (C$_2$H$_5$O)$_3$Si(CH$_2$)$_3$Cl<br>(CH$_3$O)$_3$Si(CH$_2$)$_3$Br | Nucleophiles (to displace halogen) |
| Isocyanate functional group | |
| (C$_2$H$_5$O)$_3$Si(CH$_2$)$_3$NCO<br>(CH$_3$O)$_2$(CH$_3$)SiCH$_2$NCO | Alcohols, Amines (any nucleophile), Iocyanate, Dienes |
| Sulfur functional group | |
| (C$_2$H$_5$O)$_3$Si(CH$_2$)$_3$SH<br>(CH$_3$O)$_3$Si(CH$_2$)$_{11}$SH | Thiols, Halogens, Transition metal ions |
| Vinyl and olefin functional group | |
| (CH$_3$O)$_3$SiCH$_2$CH=CH$_2$<br>(C$_2$H$_5$O)$_3$Si(CH$_2$)$_{20}$CH=CH$_2$ | Alkyls, Aryls, Halogens, Alkenes, Alkynes |

According to the disclosure, $R^1$ is a non-antibody moiety or an antibody moiety. In some embodiments, the non-antibody moiety or antibody moiety is complexed to a target. In other embodiments, the non-antibody moiety or antibody moiety is not complexed to a target. Preferred non-antibody moieties and antibody moieties, and their preferred targets, are set forth in Tables 2 and 3.

TABLE 2

| Non-antibody moieties | Target |
| --- | --- |
| biotin | avidins |
| Arg-Gly-Asp (RGD) | cellular adhesion molecules, e.g., αvβ3-integrin |
| cyclic Arg-Gly-Asp | cellular adhesion molecules, e.g., αvβ3-integrin |
| Asn-Gly-Arg | aminopeptidase N |
| folate | folate receptors |
| transferrin | transferrin receptors |
| granulocyte-macrophage colony stimulating factor (GM-CSF) | GM-CSF receptors |
| galactosamine | galactosaminereceptors on hepatocytes |
| hyaluronic acid | hyaluronic acid receptors |
| HERPBK10 | heregulin receptors |
| CCK8 | cholescystokinin |
| F3 | nucleolin |
| $^{18}$F-glucose | cell metabolism |

TABLE 3

| Antibody Moieties | Target |
| --- | --- |
| anti-VEGFR | vasculature endothelial growth-factor receptors |
| anti-ERBB2 | ERBB2 receptors |
| anti-CD19 | CD19, a pan-B-cell surface epitopes |
| anti-CD20 | CD20, a B-cell surface antigen |
| anti-CD22 | CD22, a B-cell surface antigen |
| anti-CD25 | CD25, α-subunit of the interleukin-2 receptors |
| anti-CD33 | CD33, a sialo-adhesion moleculr or a T-cell epitopes |
| anti-HLA-DR10b | HLA-CR10β subunit |
| anti-tenascin | extracellular-matrix proteins |
| anti-CEA (carcinoembryonic antigen) | CEA |
| anti-MUC1 | MUC1, an aberrantly glycosylated epithelial mucins |
| anti-TAG72 (oncofetal antigen tumor-associated glycoprotein-72) | TAG72, oncofetal antigen tumor-associated glycoprotein-72 |

See also, Allen, T.M. Nature Rev. Cancer 2002, 2, 750; Accardo, A. et al. Polymer J. 2013, 45, 481; Aina, O.H. et al. Biopolymers 2002, 66, 184; Jaracz, S. et al. Bioorg. Med. Chem. 2005, 13, 5043; Jin, S.-E. et al. BioMed. Res. Intl. 2014, 814208.

Preferably, the materials used in the imaging methods of the disclosure include

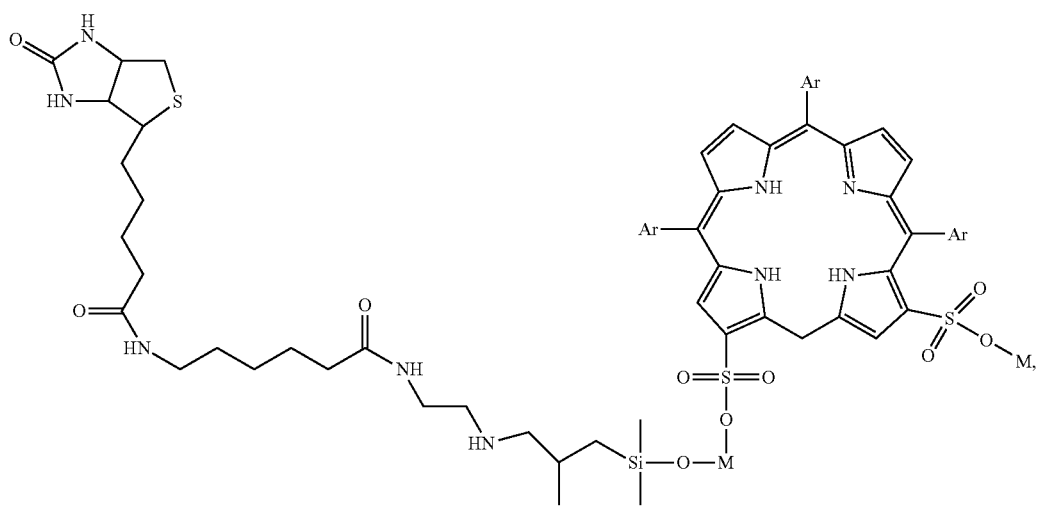

-continued
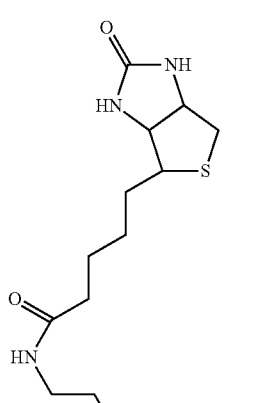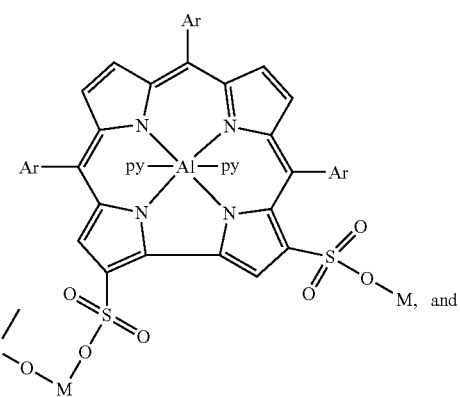M, and
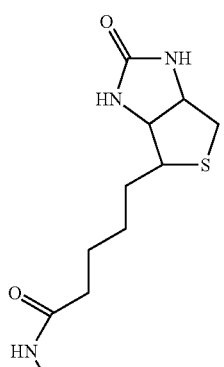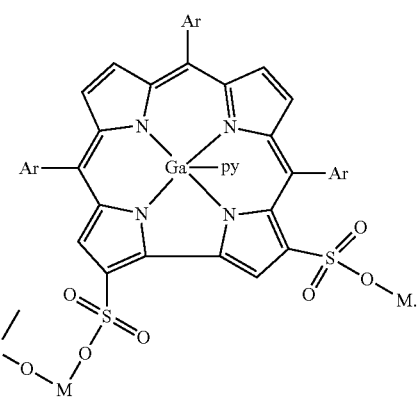M.

Preferably, Ar is pentafluorophenyl and M is preferably TiO$_2$.

The disclosure is also directed to materials according to formula II:

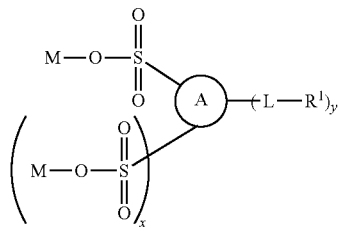

II wherein A is a corrolyl or metallated corrolyl;

M is a surface comprising TiO$_2$, BaTiO$_3$, SnO$_2$, Al$_2$O$_3$, Fe$_2$O$_3$, Fe$_3$O$_4$, ZrO$_2$, CeO$_2$, CdO, Cr$_2$O$_3$, CuO, MnO, Mn$_2$O$_3$, MnO$_2$, NiO, SnO, SnO$_2$, SiO$_2$, or ZnO;

L is a linker;

R$^1$ is a non-antibody moiety or an antibody moiety, wherein the non-antibody moiety or the antibody moiety is optionally complexed to a target;

y is 1, 2, or 3; and x is 0 or 1.

Within the scope of the disclosure, M is a surface that comprises a metal oxide, for example, a metal oxide that comprises at least one —OH group. The —OH group can be inherently present on the surface. Alternatively, the at least one —OH group can be incorporated by oxidizing the surface with a reagent such as hydrogen peroxide. Preferred surfaces for use in the disclosure include TiO$_2$, BaTiO$_3$, SnO$_2$, Al$_2$O$_3$, Fe$_2$O$_3$, Fe$_3$O$_4$, ZrO$_2$, CeO$_2$, CdO, Cr$_2$O$_3$, CuO, MnO, Mn$_2$O$_3$, MnO$_2$, NiO, SnO, SnO$_2$, SiO$_2$, and ZnO. In some embodiments, the surface comprises TiO$_2$. In some embodiments, the surface comprises BaTiO$_3$. In some embodiments, the surface comprises SnO$_2$. In some embodiments, the surface comprises Al$_2$O$_3$. In some embodiments, the surface comprises Fe$_2$O$_3$. In some embodiments, the surface comprises Fe$_3$O$_4$. In some embodiments, the surface comprises ZrO$_2$. In some embodiments, the surface comprises CeO$_2$. In some embodiments, the surface comprises CdO. In some embodiments, the surface comprises Cr$_2$O$_3$. In some embodiments, the surface comprises CuO. In some embodiments, the surface comprises MnO. In some embodiments, the surface comprises Mn$_2$O$_3$. In some embodiments, the surface comprises MnO$_2$. In some embodiments, the surface comprises NiO. In some embodiments, the surface comprises SnO. In some embodiments, the surface comprises SnO$_2$. In some embodiments, the surface comprises SiO$_2$. In some embodiments, the surface comprises ZnO.

In preferred embodiments, the surface is a nanoparticle surface. In other preferred methods of the disclosure, the surface comprises TiO$_2$.

Preferred corrolyls and metallated corrolyls for use in materials of formula II include those discussed previously with respect to the materials of formula I. In preferred embodiments, the corrolyl is selected from

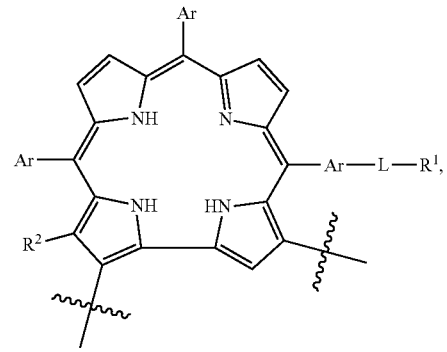

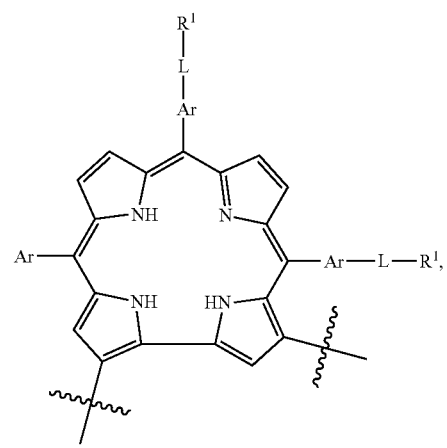

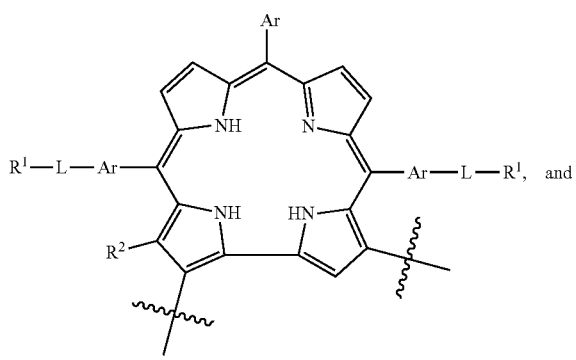

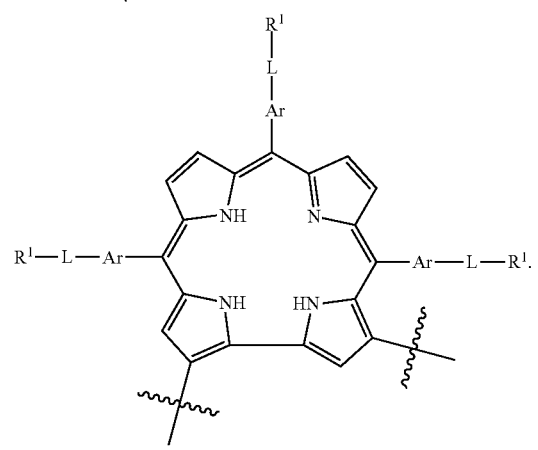

Preferred metallated corrolyls include

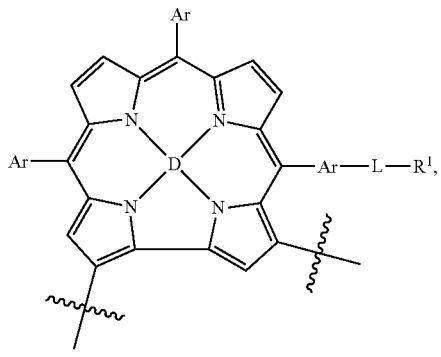

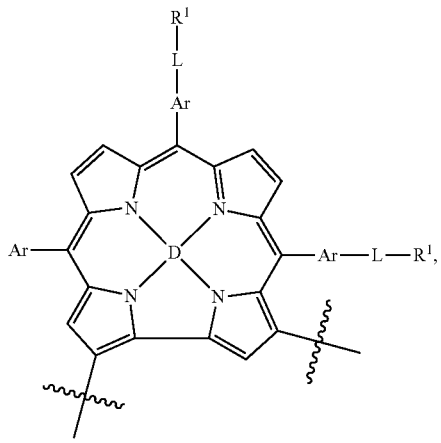

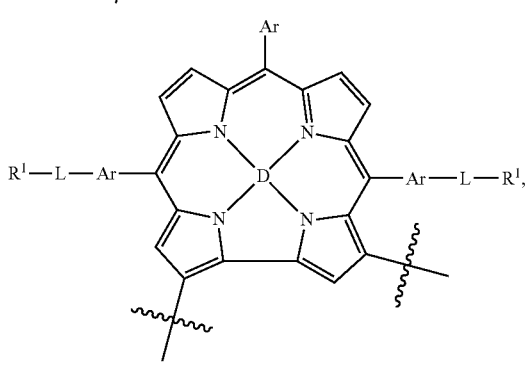

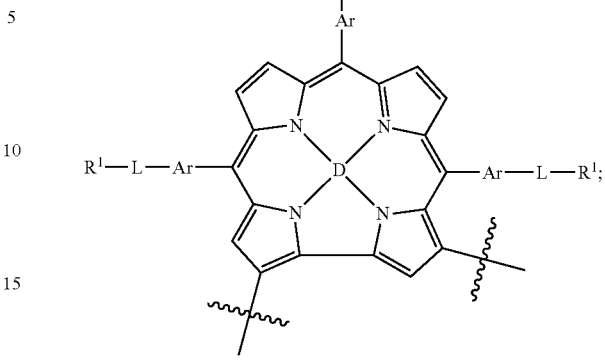

wherein D is Al, Ga, Fe, Mn, Sb, Co, Cr, Rh, Ru, Ro, Ir, V, Re, Cu, Sn, Ge, Ti, or Mo, each of which is optionally coordinated to one or more ligands. In preferred embodiments, D is Al(ligand)$_2$ or Ga(ligand). A preferred ligand is pyridine.

In preferred embodiments, x is 0. In other embodiments, x is 1.

In some embodiments, y is 1. In other embodiments, y is 2. In yet other embodiments, y is 3.

According to the disclosure, L is a linker moiety. Any suitable linker, preferably an aminoalkyl linker, can be used within the scope of the invention. A preferred L moiety is

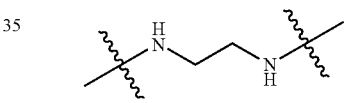

According to the disclosure R$^1$ is a non-antibody moiety or an antibody moiety. In some embodiments, the non-antibody moiety or antibody moiety is complexed to a target. In other embodiments, the non-antibody moiety or antibody moiety is not complexed to a target. Preferred non-antibody moieties and antibody moieties, and their preferred targets, are set forth above in Tables 2 and 3.

Preferred materials of formula II include:

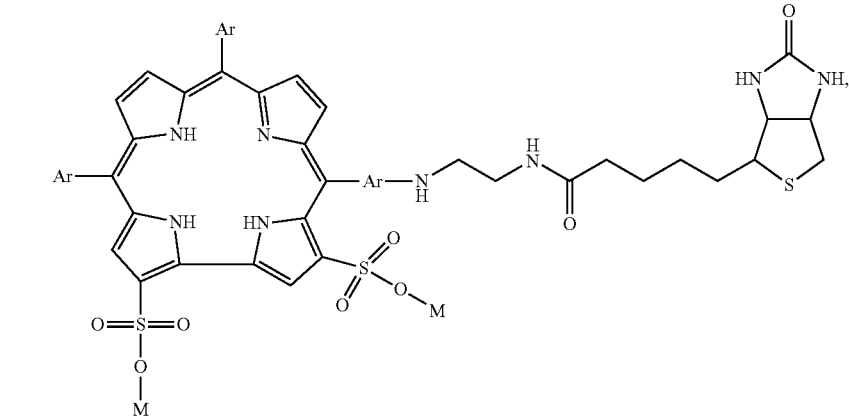

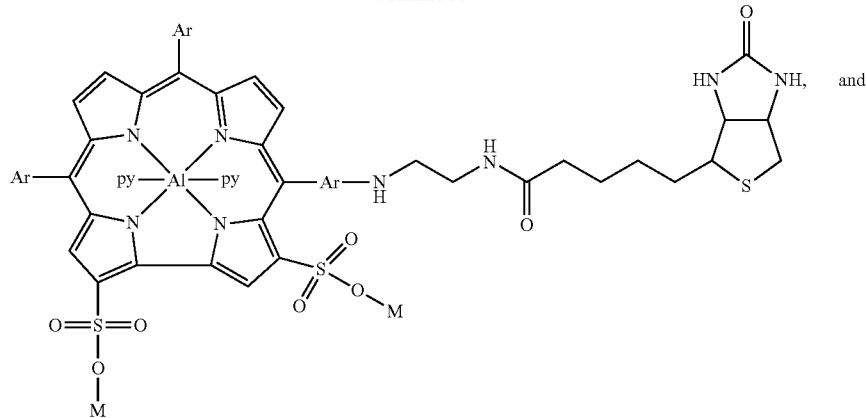
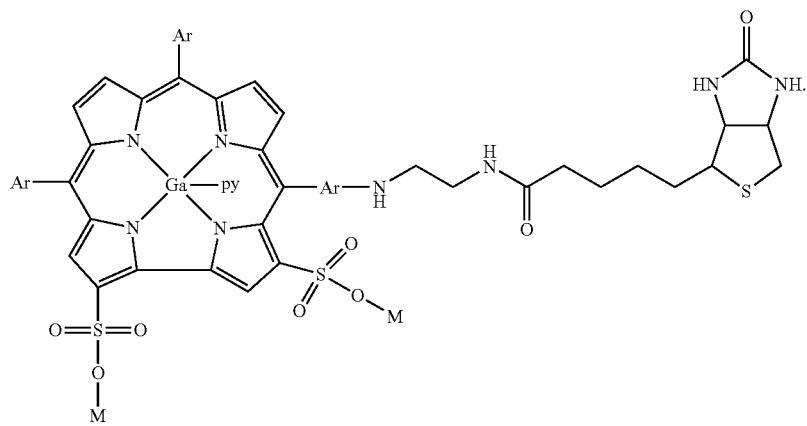
Other preferred materials for formula II include:
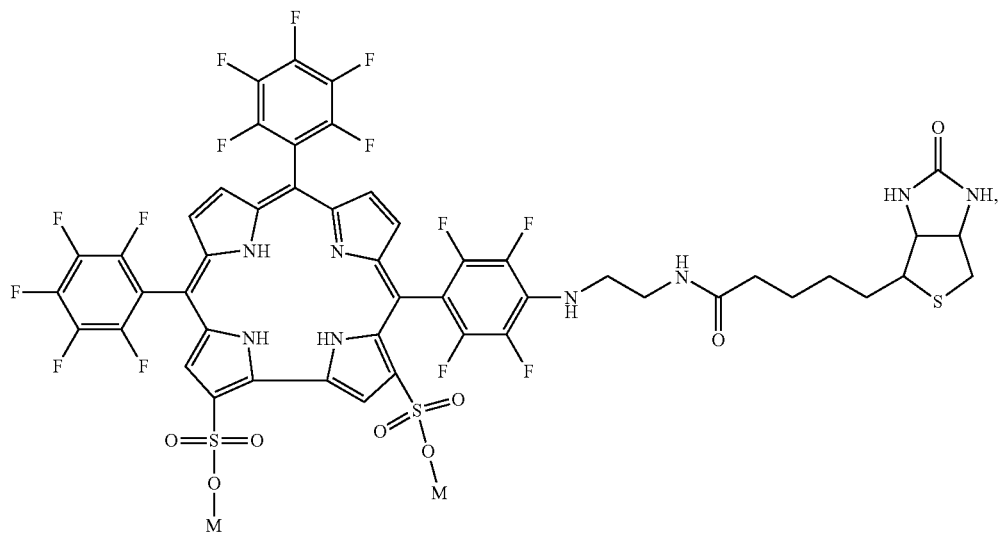

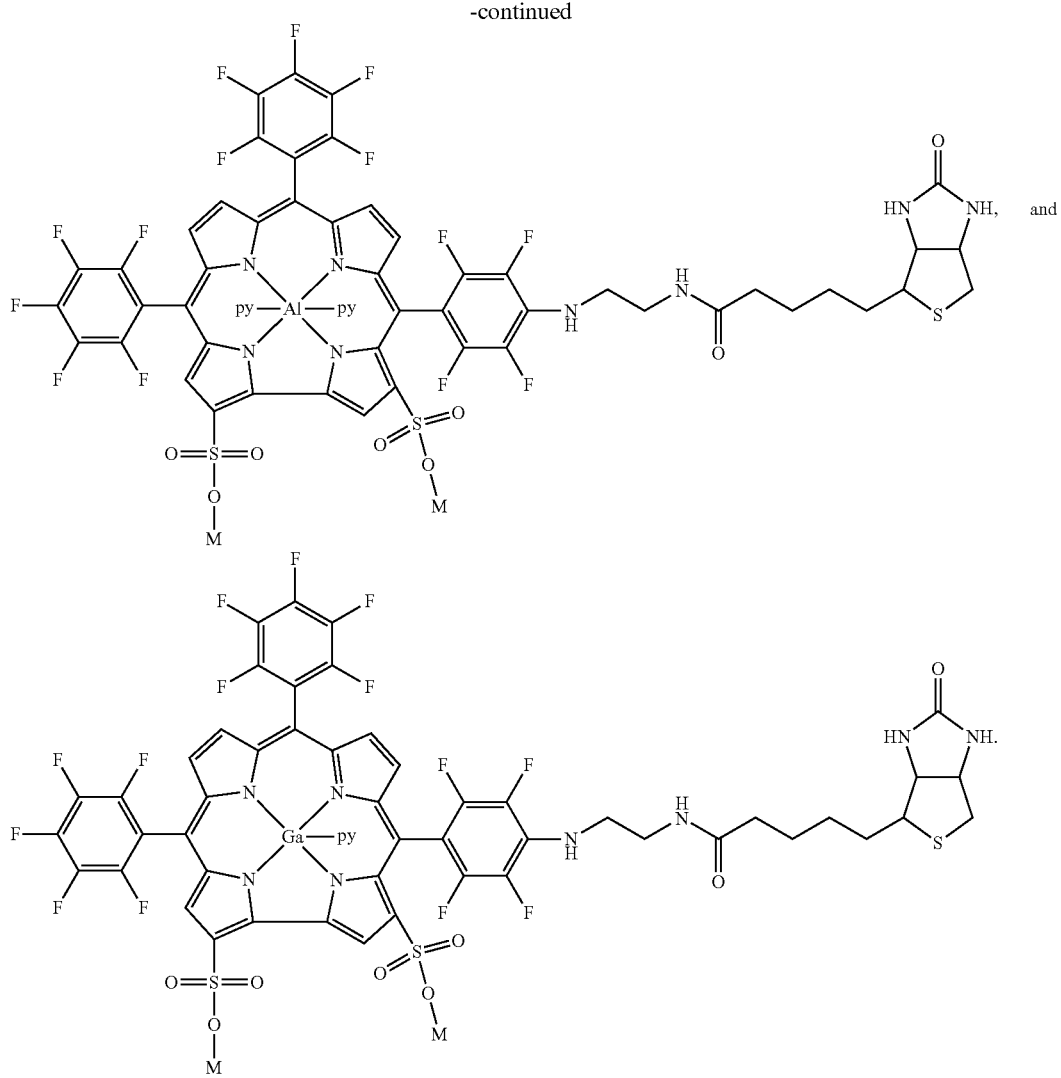

The materials of the disclosure can be used in synthetic, biomedical, and optical imaging applications. In a preferred embodiment of the disclosure, the materials of formula I or formula II are used in imaging tissues in a patient. Preferred tissues for imaging include any animal tissue, for example, bone, bone marrow, neural tissue, fibrous connective tissue, cartilage, muscle, vasculature, skin, adipose tissue, blood, and glandular tissue. Tissues from specific organs are also envisioned within the scope of the tissues that can be imaged, for example, brain, kidney, liver heart, bone, pancreas, and prostate. In some embodiments, the tissue can be cancerous tissue. In preferred methods, a material according to formula I or formula II, wherein A is a metallated corrolyl, is administered to a patient. After a period of time sufficient for the material to be taken up by the target tissue, the tissue within the patient is imaged using, for example, optical imaging, preferably fluorescence imaging. Other imaging techniques include magnetic resonance imaging (MRI) and positron emission tomography (PET). As those skilled in the art readily appreciate, different imaging techniques necessitate different metallated corrolyl moieties. For example, a preferred metal for use in MRI is manganese. A preferred metal for use in PET is $AlF_2$ or $SbF_2$. Cancers that can be imaged using the methods of the disclosure will include glioblastoma, melanoma, breast cancer, liver cancer, and colon cancer.

In other embodiments, the materials of formula I or formula II can be used in biomedical applications, for example, by selective appropriate target moieties. In one embodiments, the target moiety is an RGD peptide moiety. When incorporated into the materials of formula I or formula II, the RGD peptide moiety-modified materials of the invention can target an integrin receptor on a cancer cell surface. See, e.g., Tables 2 and 3. Other biomedical applications will be readily appreciated by those skilled in the art, in view of the present disclosure.

The materials of formula I or formula II of the disclosure are useful in corrole-based sensing applications and dye-sensitized solar cells. In other embodiments, the materials of formula I or formula II of the disclosure will have anticancer activity or will prevent cell death. In other embodiments, the materials of the disclosure are useful in singlet oxygen sensitization. In other embodiments, the materials of the disclosure are useful in lipo-protein protection and neuro-protection.

As used herein, the term "halogen" refers to F, Cl, Br, or I.

As used herein, "alkyl" refers to branched or straigh-chain saturated aliphatic hydrocarbon groups having the specified number of carbon atoms. For example, $C_{1-10}$alkyl denotes an alkyl group having 1 to 10 carbon atoms. Preferred alkyl groups include methyl, ethyl, propyl, butyl, sec-butyl, tert-butyl, pentyl, hexyl, and the like.

As used herein "alkenyl" refers to hydrocarbon chains that include one or more double bonds.

As used herein, "aryl" refers to phenyl or naphthyl.

As used herein, "alkaryl" refers to an aryl moiety attached through an alkylene group, for example, benzyl (—$CH_2$-phenyl).

As used herein, "heterocycloalkyl" refers to a 5 to 7-membered monocyclic or bicyclic saturated ring that includes at least one heteroatom that is N, O, or S. Examples include piperidinyl, piperazinyl, morpholinyl, and pyrrolidinyl.

As used herein, "corrolyl" refers to a corrole moiety.

Materials of the disclosure may be prepared according to the sequence depicted in Scheme 1. As shown in sequence (A), exposed hydroxyl groups on the corrole-conjugated surface are treated with a cyclic azasilane, resulting in the formation of amines above the metal surface, which are then available for coupling. Functionalization of the corrole via nucleophilic aromatic substitution is depicted in sequence (B). The freebased conjugates can be heated to reflux in ethylene diamine to provide amine termini at the para-positions of the pentafluorophenyl groups. Both system can then be treated with, for example, EX-Link Biotin NHS to afford the NHS conjugate. The bioconjugated species can then be treated with a target, for example Streptavidin-Alexfluor-488 and visualized using confocal fluorescence microscopy. See FIGS. 1 and 2.

Scheme 1A

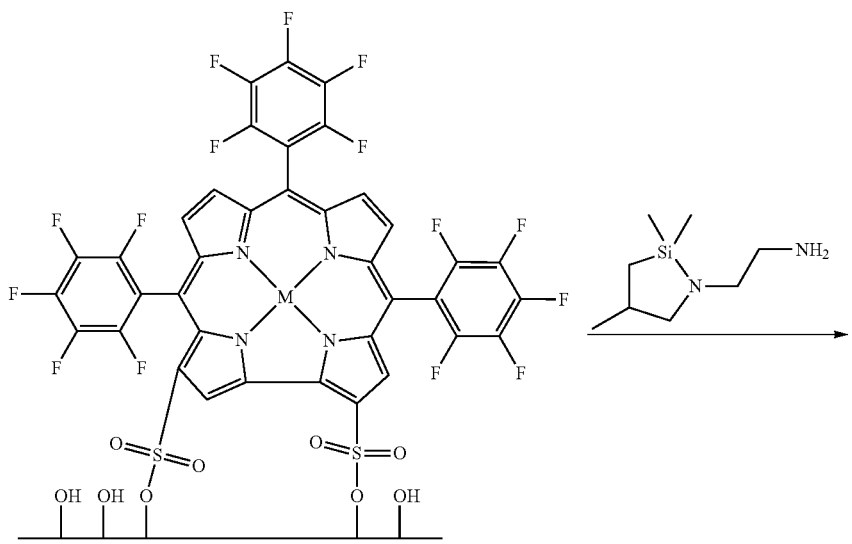

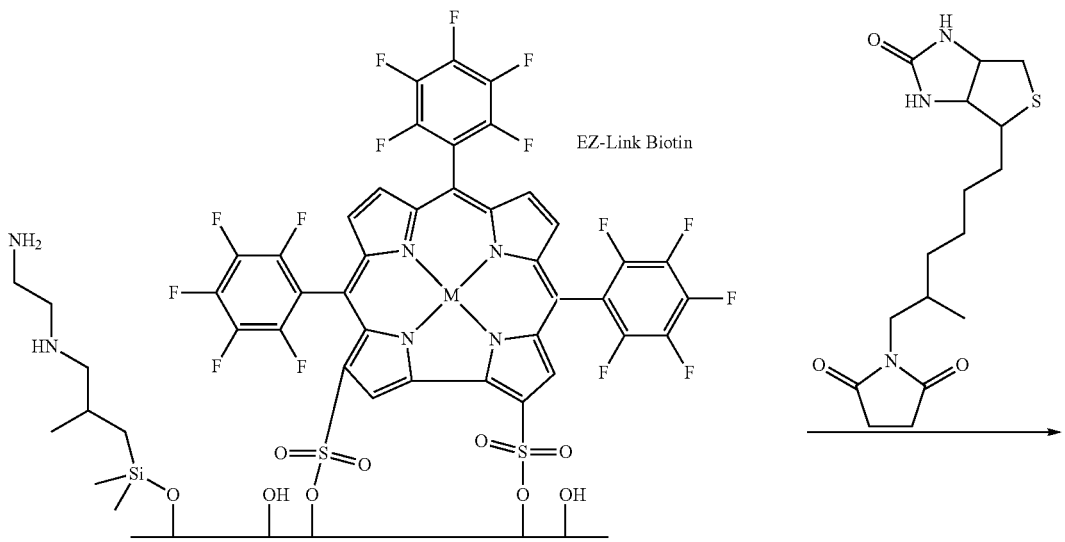

-continued
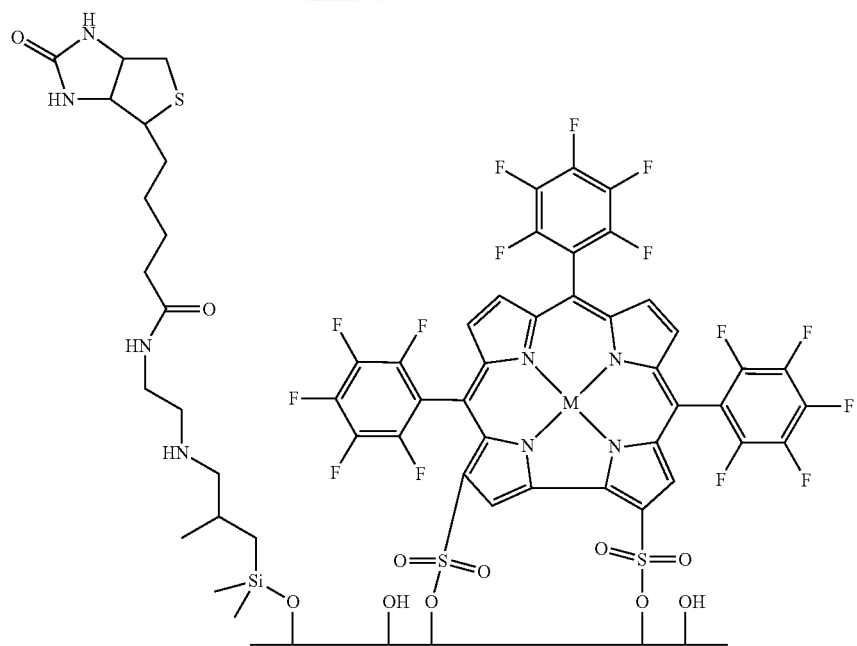
Scheme 1B
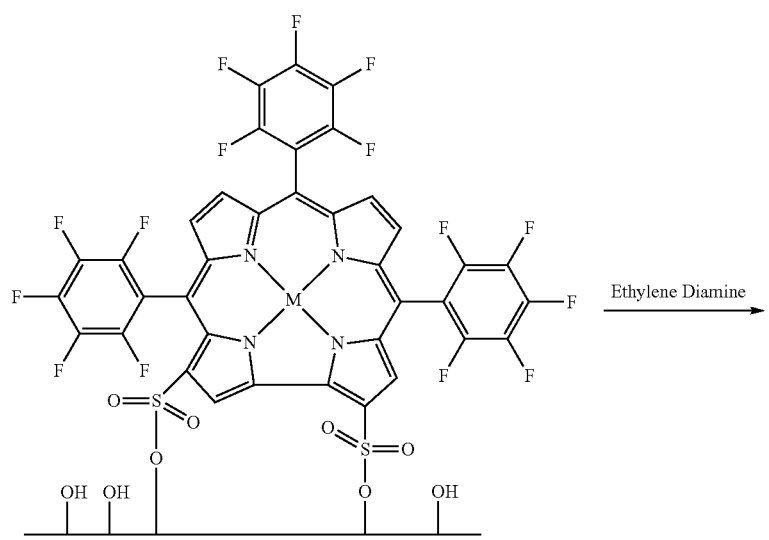
Ethylene Diamine →

31
-continued
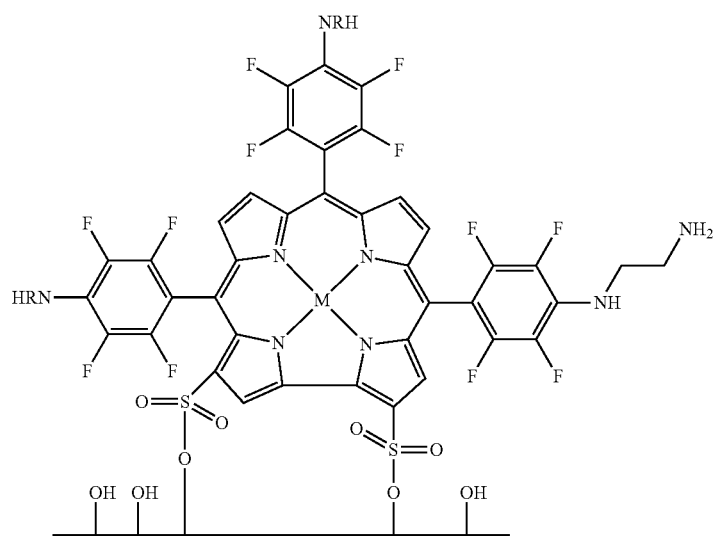
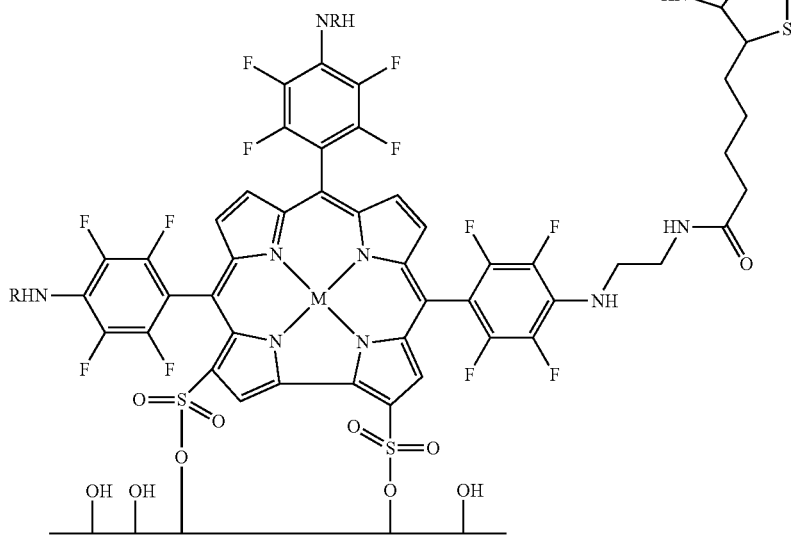
The following examples are presented in order to more fully illustrate the preferred embodiments of the disclosure. They should in no way be construed, however, as limiting the broad scope of the disclosure.
EXPERIMENTAL SECTION
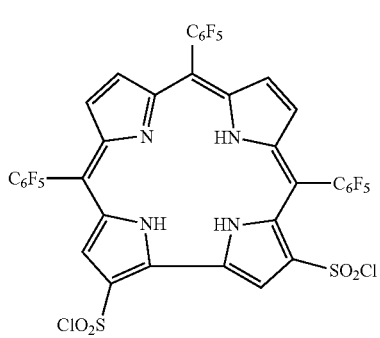
1
32
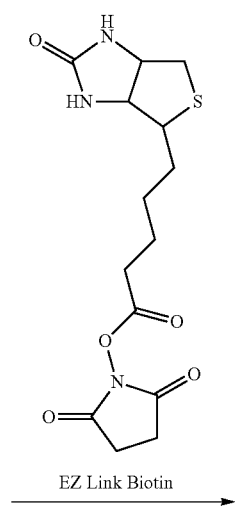
EZ Link Biotin
-continued
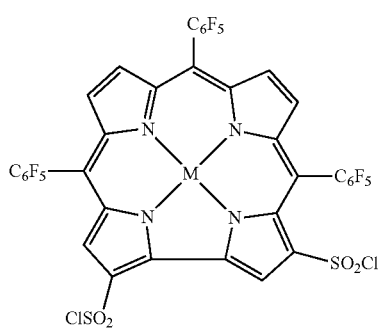
M = Al(py)$_2$ or Ga(py)
py = pyridine

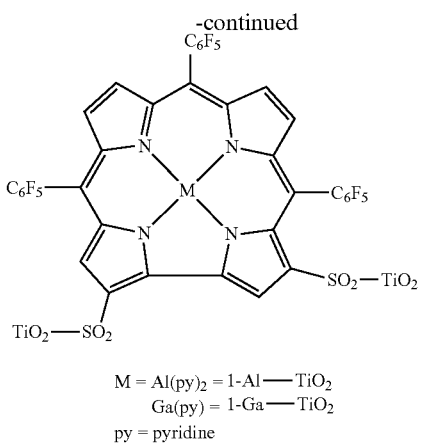

M = Al(py)$_2$ = 1-Al—TiO$_2$
Ga(py) = 1-Ga—TiO$_2$
py = pyridine

Materials. 2 M AlMe$_3$ in toluene (Aldrich), GaCl$_3$ (Aldrich), HSO$_3$Cl (Aldrich), 21 nm nanopowder TiO$_2$ (Aldrich), 30% H$_2$O$_2$ (EMD) were obtained commercially and used as received. The starting material 5,10,15-tris(pentafluorophenyl) corrole (H$_3$tpfc) was prepared based on the literature method. The solvents pyridine and toluene were dried over a column. Acetone and dichloromethane used were both of reagent and spectroscopic grades depending on the applications. D-Luciferin potassium salt (Promega), Hoechst 34580 (Invitrogen™), Hoechst 33258 (Invitrogen™), Sytox Green (Invitrogen™), and FM® 1-43FX (Invitrogen™) were used as received according to the provider's instruction.

Chemical Preparation. All preparations were carried out under Ar(g) atmosphere unless otherwise noted.

1. Corrole Preparation. Preparation of 2,17-bischlorosulfonato-5,10,15-tris(pentafluorophenyl) corrole (H$_3$tpfc (SO$_2$Cl)$_2$; 1) was performed according to the literature procedure. The metallocorroles described in this study were prepared in the following manner.

1.1. Preparation of 1-Al. To the 20-mL toluene solution of 0.32 g of 1 (0.32 mmol) in a round bottom flask was added 0.8 mL of 2 M AlMe$_3$ (1.6 mmol) in toluene solution at an icebath temperature. The solution was stirred for 10 min followed by the addition of 1 mL anhydrous pyridine. The solution was allowed to stir for another 10 min over ice. The reaction was quenched by an addition of ice chips. The dark green solution was then extracted with CH$_2$Cl$_2$ and washed with water. The solvent was removed in vacuo and the dry deep green solid was redissolved in CH$_2$Cl$_2$ followed by filtration. The filtrate was brought to dryness to afford the dark green solid (0.098 g, 26% yield). ESI-MS (CH$_2$Cl$_2$): m/z: 1014.87 [M-H]$^-$ (Calculated for C$_{37}$H$_6$N$_4$F$_{15}$Cl$_2$S$_2$O$_4$Al: 1015.88); $^1$H-NMR (400 MHz, acetone-d$_6$, ppm): δ=9.76 (s, 1 H), 9.25 (s, 1 H), 8.97 (d, 1 H), 8.85 (d, 1 H), 8.70 (d, 1 H), 8.58 (d, 1 H); 19 F-NMR (376 MHz, acetone-d6, ppm): −138.7 (d, 4 F), −140.0 (d, 2 F), −156.9 (t, 1 F), −157.5 (t, 1 F), −158.1 (t, 1 F), −164.9 (m, 2 F), −165.3 (m, 2 F), −167.0 (m, 2 F); UV-Vis (toluene:pyridine, 95:5): λmax (ϵ M$^{-1}$ cm$^{-1}$)=436 (4.08×10$^4$), 625 (7.66×10$^3$) nm.

1.2. Preparation of 1-Ga. To a heavy-walled Schlenk flask were added 0.20 g of 1 (0.20 mmol) and 0.57 g GaCl$_3$ (3.3 mmol) under Ar(g). The flask was chilled in N$_2$(l) and evacuated. 15 mL Degassed anhydrous pyridine (15 mL) was added to the flask via vacuum transfer. The flask was subsequently sealed and allowed to warm to room temperature. The reaction vessel was heated to 120° C. for 1 h. The pyridine solution was diluted with CH$_2$Cl$_2$ and washed with water three times. The solution was then filtered through glass wool and partially concentrated for recrystallization with hexanes overnight. The product was then filtered, dried, and washed with a combination of acetone, CH$_2$Cl$_2$, and toluene. This filtrate collected was brought to dryness in vacuo to afford a dark green solid (0.092 g, 38% yield). ESI-MS (CH$_2$Cl$_2$:pyridine): m/z: 1056.81 [M-H]$^-$ (Calculated for C$_{37}$H$_8$N$_4$F$_{15}$Cl$_2$S$_2$O$_4$Ga: 1057.82); $^1$H-NMR (500 MHz, CD$_2$Cl$_2$, ppm): δ=9.99 (s), 8.82 (m), 8.73 (m), 8.57 (m); $^{19}$F-NMR (376 MHz, acetone-d$_6$, ppm): −138.7 (d), −140.0 (d), −156.9 (t), −157.5 (t), −158.1 (t), −164.9 (m), −165.3 (m), −167.0 (m); UV-vis (toluene:pyridine, 95:5): λmax (ϵ M$^{-1}$ cm$^{-1}$)=429 (1.65×10$^4$), 611 (5.61×10$^3$) nm.

2. TiO$_2$ Surface activation. To the solid TiO$_2$ nanoparticle (10 g) in a 2.0-L round bottom flask was added 1.2 L 30% H$_2$O$_2$ solution. The milky colloidal suspension was stirred under reflux or 5 h. Upon cooling, the off-white solid was isolated from the H$_2$O$_2$ solution by ultracentrifugation at 4° C. and washed with copious amount of water. The activated TiO$_2$ nanoparticle (TiO$_2$—OH) collected was dried in vacuo for 12 h and stored dry in a vial prior to use.

3. Surface Conjugation. The following general procedure was employed for the conjugation of the corroles 1, 1-Al, and 1-Ga to the activated TiO$_2$ nanoparticle surface: To the mixed solids containing the activated TiO$_2$ and corrole in a 25-mL round bottom flask was charged with anhydrous pyridine. The suspension turned green immediately and was stirred under reflux before the reaction was stopped. The resulting green solid was isolated from the green solution by centrifugation and washed multiple times with dichloromethane, acetone, and deionized water until the centrifuge supernatant became colorless. The solid remained green, was dried in vacuo, and was stored until further use. The detailed preparation procedure for each corrole nanoconjugate is given as follows:

3.1. Preparation of 1-TiO$_2$. To a 25 mL round bottom flask were added 0.32 g TiO$_2$—OH and 0.028 g of 1 (28.1 μmol), which was subsequently cycled with argon and vacuum. After establishment of the inert atmosphere, 8 mL anhydrous pyridine was added to the flask and the reaction was set to reflux for 2 h. The resulting green solid was collected in a manner following the general centrifugation and washing procedures outlined above.

3.2. Preparation of 1-Al—TiO$_2$. To a 40 mL vial was added 1.18 g TiO$_2$—OH, which was subsequently cycled with argon and vacuum. To this flask, was added 5 mL anhydrous pyridine, followed by sonication to ensure even dispersion. In a second flask, was added 0.03 g of 1-Al (25.5 μmol) and 7 mL anhydrous pyridine under Ar(g). This solution was stirred and then added to the TiO$_2$—OH precursor via syringe. The reaction was sealed and allowed to reflux for 2 h after which, the resulting green solid was collected in a manner following the general centrifugation and washing procedures outlined above.

3.3. Preparation of 1-Ga—TiO$_2$. To a 40 mL vial was added 0.84 g TiO$_2$—OH and 0.04 g of 1-Ga (32.8 μmol), which was subsequently cycled with argon and vacuum. After establishment of the inert atmosphere, 8 mL anhydrous pyridine was added to the flask and the reaction was set to reflux for 2 h. The resulting green solid was collected in a manner following the general centrifugation and washing procedures outlined above.

Spectroscopies. UV-vis spectra were either recorded on a Carey 50 spectrophotometer or a Hewlett-Packard 8453 diode-array spectrophotometer at room temperature from samples in various solvents. IR spectra were recorded with a SensIR Durascope ATR accessory plate on a Nicolet Magna-IR spectrometer, an uncooled pyroelectric deuterated triglycine sulfate (DTGS) etector, and a KBr beamsplitter. The $^1$H and $^{19}$F NMR spectra were recorded on a Varian Mercury 300 (300 MHz for 1H; 288 MHz for $^{19}$F) spectrometer. The NMR spectra were analyzed using MestReNova (v. 6.1.1). $^1$H NMR measurements were referenced to internal solvents. Fluorescence spectra were measured with a Jobin-Yvonne/SPEX Fluorolog spectrometer (Model FL3-11) equipped with a Hamamatsu R928 PMT. Samples were excited at λex=405-430 nm (the Soret region), 514 nm, and 600-630 nm (Q-band region) with 2-nm band-passes. The fluorescence was observed from λem=500-800 nm, depending on the excitation wavelength, at 2-nm intervals with 0.5 s integration times at room temperature.

Relative Fluorescence Quantum Yield Measurements. The Φem measurements were performed using degassed toluene solutions of 1, 1-Al, 1-Ga, and tetraphenylporphyrin (as a standard). Samples were excited at λex=355 nm and the emission was observed from λem=500-800 nm. The standard tetraphenylporphyrin was excited at λex=514 nm and the emission was observed from λem=500-800 nm. diem for tetraphenylporphyrin is 0.11.3 All relative fluorescence quantum yields were calculated based on the corresponding fluorescence spectra of the samples and the standard according to the equation:

$$\phi_{em}(x) = \frac{A_s \cdot F_x \cdot \eta_x^2 \phi_{em}(s)}{A_x \cdot F_s \cdot \eta_s^2}$$

where Φem(s) and Φem(x) are the relative fluorescence quantum yield of the standard and sample, respectively; As and Ax are the absorbance at the excitation wavelength for the standard and sample, respectively; Fs and Fx are the area under the corrected emission curve for the standard and sample, respectively; and ηs and ηx are the refractive index of the solvent used for the standard and sample, respectively.

Mass Spectrometry. Samples were analyzed by direct infusion ESI in the negative ion mode using an LCT Premier XE (Waters) ESI-TOF mass spectrometer operated in the W configuration. The samples were prepared in CH2Cl2:isopropanol (9:1 v/v) at ≈10 μM and infused with an external syringe pump at 25 μL/min. Some samples contained 50 μL pyridine in 1 mL $CH_2Cl_2$:isopropanol mixture.

Surface characterization. X-ray photoelectron spectroscopy was performed on an M-Probe spectrometer that was interfaced to a computer running the ESCA2005 (Service Physics) software. The monochromatic X-ray source was the 1486.6 eV Al Kα line, directed at 35° to thesample surface. Emitted photoelectrons were collected by a hemispherical analyzer that was mounted at an angle of 35° with respect to the sample surface. Low-resolution survey spectra were acquired between binding energies of 1 and 1100 eV. Higher-resolution detailed scans, with a resolution of 0.8 eV, were collected on the F(1s) XPS line. All binding energies are reported in electronvolts.

Figure 8:
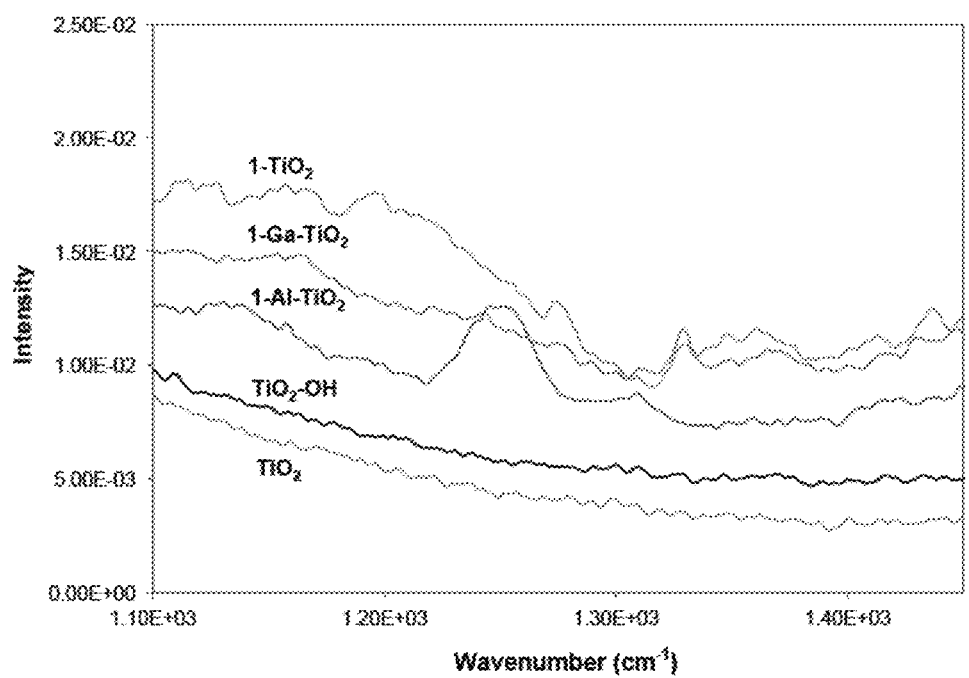
FIG. 8 depicts ATR-IR spectra for $TiO_2$ nanoparticles and preferred materials of the invention.
Figure 9:
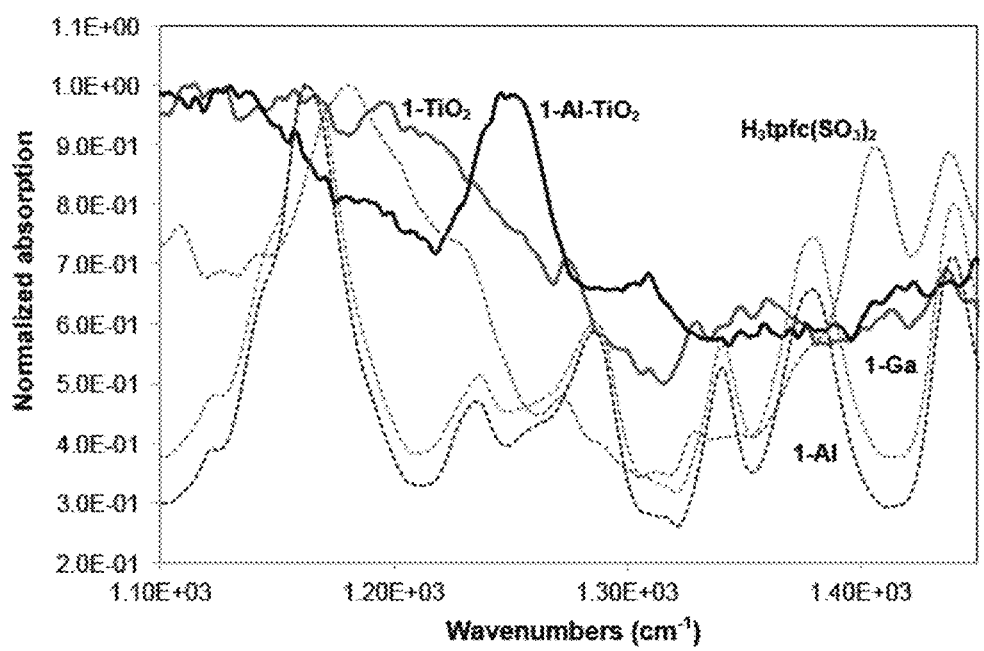
FIG. 9 depicts normalized ATR-IR spectra for $TiO_2$ nanoparticles and preferred materials of the invention.

Attenuated total reflectance (ATR) infrared spectra of powdered corrole-$TiO_2$ nanoconjugate samples were collected using a SensIR Durascope ATR accessory plate on a Nicolet Magna-IR spectrometer, an uncooled pyroelectric deuterated triglycine sulfate (DTGS) detector with a KBr window (400-4000 $cm^{-1}$), and a KBr beamsplitter. The spectral resolution was 4 $cm^{-1}$ and 64 scans were collected per spectrum. A KBr background spectrum was subtracted from the measured spectrum of the nanoconjugates to provide the desired FTIR characterization data. See FIGS. 8 and 9.

Confocal Microscopy. The phantom imaging experiments were performed using a Zeiss LSM 710 Confocal Microscope (Carl Zeiss, Wake Forest, N.C.). The microscope system consists of a Zeiss 710 confocal scanner, 63×/1.4 Plan-APOCHROMAT oil immersion lens (Zeiss), Axio Observer Z1 microscope and diode-pump solid-state lasers. Two visible excitation lines (405 and 561 nm) were used for the experiments. The microscope is equipped with a QUASAR 32 channel spectral detector (two standard PMTs and a 32 channel PMT array) with spectral resolution of 9.7 nm. The software ZEN 2009 was used for hardware control. The laser power used for the experiments is 10% of the total available power (25 mW). ImageJ software was employed to process the resulting data.

Transmission electron microscopy. The morphologies of the TiO2 nanoparticles before and after surface functionalization were imaged using a FEI Tecnai F30ST transmission electron microscope (TEM) operated at acceleration voltage of 300 kV. Images were recorded using a Gatan CCD camera. For TEM analysis, a small quantity of TiO2 particles was dispersed in IPA by sonication. The dispersions were drop-cast onto C-flatTM holey carbon films on a 200 mesh Cu TEM grid (purchased from Electron Microscopy Sciences).

Approximation of loading of 1-Al on $TiO_2$ surface. Calculation of the corrole 1-Al's loading on the surface of $TiO_2$ was based on the absorbance values obtained from the integrated sphere electronic absorption measurements described as follows.

Figure 3:
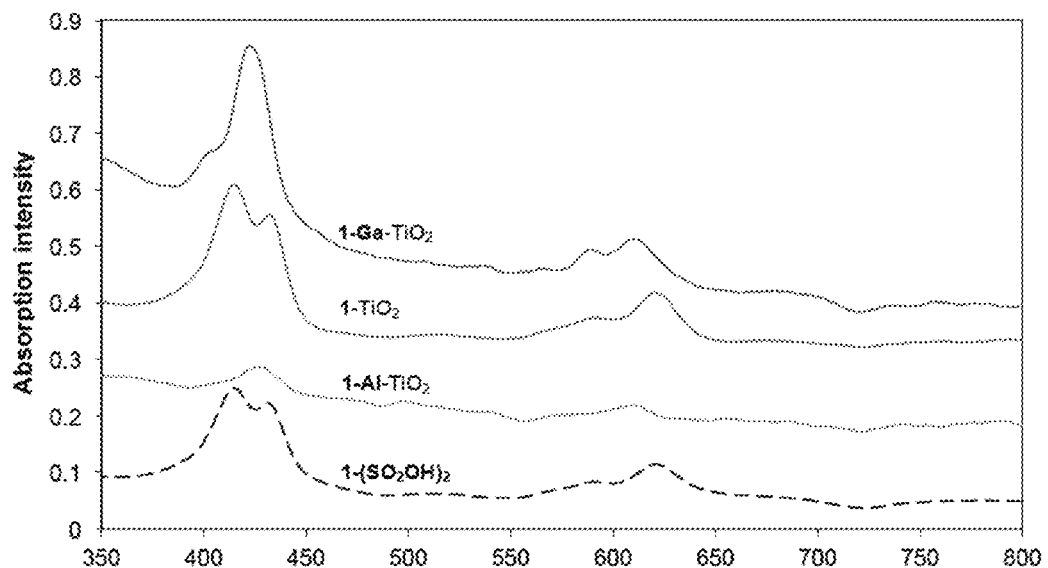
FIG. 3 depicts electronic absorption spectra for an amphiphilic corrole ($H_3tpfc(SO_2OH)_2$) and corrole-$TiO_2$ nanoconjates of the invention in phosphate buffer saline pH 7.4.

Absorption spectroscopy. Thin film transflectance measurements were used to calculate the dye loading on the $TiO_2$ nanoparticles. Both peroxide-etched and dye-functionalized nanoparticles were dispersed in a polydimethylsiloxane (PDMS) polymer matrix. The weights of the $TiO_2$ nanoparticles, PDMS base (Sylgard® 184 silicone elastomer base from Dow Corning), and curing agent (Sylgard® 184 silicone elastomer curing agent from Dow Corning) are provided in Table 4 below. The nanoparticles were first dispersed in a minimal amount of isopropanol (IPA) by sonication. The dispersion of $TiO_2$ nanoparticles in IPA was then mixed with the PDMS base and curing agent using a Vortex mixer. The mixtures were cast into films onto quartz substrates and allowed to cure in air for 12 hours followed by curing in a drying oven at 60° for 2 hours. See FIG. 3.

TABLE 4

Weights of TiO₂ nanoparticles, weights of the PDMS base and curing agnet used to case PDMS films, weight % TiO₂ in the films, film weight, and mass of TiO₂ per volume of PDMS.

| Sample | Mass TiO$_2$ (mg) | Mass IPA (g) | Mass PDMS base (g) | Mass PDMS curing agent (g) | Total weight (g) | Est. dry film weight (g)[a] | Weight % TiO$_2$ | Film weight (g) | Mass TiO$_2$/ volume PDMS (g/L)[b] |
|---|---|---|---|---|---|---|---|---|---|
| Etched TiO$_2$ | 3.35 | 3.683 | 0.9266 | 0.1220 | 1.4203 | 1.0593 | 0.32 | 0.2901 | 3.3 |
| 1-Al—TiO$_2$ | 3.25 | 3.234 | 0.9425 | 0.1154 | 1.3846 | 1.0676 | 0.30 | 0.3384 | 3.2 |

[a]Separate measurements showed that 98% of the IPA evaporated during curing of the PDMS film.
[b]A value of 0.965 g/cm³ was used for the density of PDMS.

Transflectance spectra of the etched and dye-functionalized TiO$_2$ nanoparticle films were measured using a Cary 5000 UV-Vis-NIR spectrometer from Agilent Technologies equipped with an integrating sphere (External DRA 1800), a PMT detector, a quartz-iodine lamp for the visible region (350-800 nm), and a deuterium lamp for the ultraviolet region (300-350 nm). Because the TiO$_2$ nanoparticles cause diffuse scattering of the incident illumination, the PDMS films were placed in the center of the integrating sphere such that both the transmitted, T, and the reflected, R, (including the spectrally reflected and diffusely scattered light) light were collected by the PMT detector. The transflectance measurements allow for the absorbance, A, of the films to be determined by $A = -\log(T+R)$. The concentration, C, of the dye within the PDMS films was then calculated using the Beer-Lambert law, $A=\epsilon Cl$, where $\epsilon$ is the extinction coefficient of the dye and $l$ is the film thickness (determined by profilometry, see below). The absorbance values at 426 and 595 nm (corresponding to the Soret and Q bands of the dye, respectively) for the PDMS film containing the dye-functionalized TiO$_2$ nanoparticles, the estimated extinction coefficients of the dye at these wavelengths, and the film thicknesses are provided in Table 5 below. The absorbance values for the PDMS film containing the unfunctionalized, peroxide-etched TiO$_2$ nanoparticles at these wavelengths are also provided, which were subtracted from the absorbance values of the dye-functionalized TiO$_2$ nanoparticles. The dyeloading was determined to be between 2.3 and 3.5 μmole of dye per grams of TiO$_2$ (based on whether the Soret or Q band was used to determine the dye concentration).

Minumal Essential Medium (DMEM) in 5% CO$_2$ at 37° C. The cell culture medium was supplemented with 10% fetal bovine serum (FBS) and 1% the antibiotic primocin. The cell culture medium was replenished every two days and the cells were passaged once they reached 80% confluence. Primary mouse hepatocytes (PMH) were isolated and cultured as previously described.

For U87-Luc cell culture experiments. The cells were plated in an 8-chamber slide (Cultureslide, BD) were treated with 1-Al—TiO2 suspended in PBS over a range of 2 ng/mL to 2 mg/mL. A primary stock solution (6.3 mg 1-Al—TiO$_2$ in 1 mL PBS) was prepared. The primary stock solution was further diluted to prepare secondary and tertiary stock solutions. The various amount of stock solutions were added to the eight-well glass slide plated with cells to give the aforementioned range of concentrations. The final volume for each well is 300 μL. After treatment, the treated cells and controls were incubated in the dark in 5% CO$_2$ at 37° C. for a period of 24, 48, and 72 h. The cells were imaged using the cooled IVIS® animal imaging system (Xenogen, Alameda, Calif. USA) linked to a PC running with Living Image™ software (Xenogen) along with IGOR (Wavemetrics, Seattle, Wash., USA) under Microsoft® Windows® 2000. This system yields high signal-to-noise images of luciferase signals emerging from the cells. Before imaging, 0.5 mL of 150 mg/mL luciferin in normal saline was added to each well. An integration time of 1 min with binning of 5 min was used for luminescent image acquisition. The signal intensity was quantified as the flux of all detected photon counts

TABLE 5

Absorption values at 426 and 595 nm and thicknesses for PDMS films containing dyefunctionalized and peroxide-etched TiO$_2$ nanoparticles, and estimated dye loading of the TiO$_2$ particles based on absorption measurements.

| Wavelength (nm) | Dye-functionalized TiO$_2$ absorbance | Film thickness (cm) | Est. dye extinction coefficient (M$^{-1}$cm$^{-1}$)[a] | Etched TiO$_2$ absorbance | Film thickness (cm) | Dye concentration (M) | Dye loading (μmoles of dye/ g of TiO$_2$) |
|---|---|---|---|---|---|---|---|
| 426 | 0.170 | 0.054 | $4.08 \times 10^4$ | 0.005 | 0.054 | $7.5 \times 10^{-5}$ | 2.3 |
| 595 | 0.048 | 0.054 | $7.66 \times 10^3$ | 0.002 | 0.054 | $1.1 \times 10^{-4}$ | 3.5 |

[a]Extinction coefficients measured in toluene:pyridine (95:5) mixture.

Profilometry. Thickness profiles of the PDMS films were measured using a Bruker DektakXT stylus surface profilometer. The diameter of the diamond-tipped stylus was 2 μm and a weight of 1 mg was applied to the film, respectively. The stylus was scanned at a rate of 250 μm/s. The thickness profiles were used measure the average path length through the PDMS films during the transflectance measurements.

Cell culture and cell viability assay. Pathogen-free U87-LUC cell line (TSRI Small Animal Imaging and Research Laboratory) was grown in 75 mL flask in Dulbecco's within each well using the LivingImage software package. All experiments were performed in triplicate.

For PMH cell culture experiments, the cells were plated in a 6-chamber slide (Cultureslide, BD). After three hours, media was exchanged (DMEM-F12) and the cells were treated with 1-Al—TiO$_2$ suspended in PBS over a range of 0.3 ng/mL to 0.3 mg/mL. A primary stock solution (6.3 mg 1-Al—TiO$_2$ in 1 mL PBS) was prepared. The primary stock solution was further diluted to prepare secondary and tertiary stock solutions. The various amount of stock solutions were added to the eight-well glass slide plated with cells to give the aforementioned range of concentrations. The final volume for each well is 2000μL. After 24 or 48 h of treatment, cells were double stained with Hoechst 33258 (8 mg/mL) and Sytox Green (1 mmol/L). Quantitation of total and necrotic cells (Sytox Green positive) was performed by counting cells in at least 5 different fields using ImageJ, as previously described. All experiments were done in triplicate.

In vitro confocal fluorescence microscopy. The U87-Luc cells were seeded at 20,000 cells per well on an 8-chamber slide (Cultureslide, BD) and allowed to grow overnight. Cells were washed with PBS and were incubated in serum free media mixed 1:1 with 1-Al—$TiO_2$ for 24, 48, and 72 h at 37° C. over the concentration range similar to the U87-Luc cell viability assay (2 ng/mL to 2 mg/mL). Cells were then washed 3× with PBS and stained with Hoechst 33258 and FM® 1-43FX stains. The cells were chilled on iced and then imaged without being fixed using a Zeiss LSM 710 inverted confocal microscope.

Electronic absorption spectra for 1, 1-Al, and 1-Ga was obtained in degassed toluene. Solutions reveal the signature Soret and Q-bands for these tetrapyrrolic macrocycles (FIG. 1). The electronic absorption data for the chlorosulfonated corroles are also given in Table 6.

TABLE 6

Electronicspectroscopic data for chlorosulfonated corroles 1, 1-Al, and 1-Ga in toluene solution

| Corrole | Electronic Absorption[a] $\lambda_{max}$[b] (nm) | Fluorescence[a] $\lambda_{ex}$ (nm) | $\lambda_{ex}$ (nm) | $\phi$em[c] |
|---|---|---|---|---|
| 1 | 430 (S) 580 (Q) | 426 | 670 | 0.094 |
| 1-Al | 424 (S) 592 (Q) | 420 | 611 | 0.127 |
| 1-Ga | 426 (S) 588 (Q) | 427 | 609 | 0.099 |

[a]The measurements were performed in degassed toluene.
[b]The maximum absorption wavelengths are reported for both Soret (S) and Q-bands (Q).
[c]The relative emission quantum yields were determined using tetraphenylporphyrin as a standard.

The electronic absorption spectra of the colloidal suspensions of 1-$TiO_2$, 1-Al—$TiO_2$, and 1-Ga—$TiO_2$ nanoconjugates in PBS pH 7.4 reveal maximum absorptions centered around 425 and 600 nm for the Soret and Q-bands, respectively (Table 7).

TABLE 7

Electronic absorption, vibrational, and X-ray photoelectron spectroscopic data for corrole-$TiO_2$ nanoconjugates 1-$TiO_2$, 1-Al-$TiO_2$, and 1-Ga-$TiO_2$

| Conjugate | Electronic Absorption $\lambda_{max}$ (nm) | $SO_2$ Vibrational Frequency ($cm^{-1}$) Sym | Asym | F(1s) Binding Energy (eV) |
|---|---|---|---|---|
| 1-$TiO_2$ | 415, 430 (S) 591, 621 (Q) | 1153 | 1410 | 691 |
| 1-Al-$TiO_2$ | 427 (S) 576, 610 (Q) | 1244 | 1431 | 690 |
| 1-Ga-$TiO_2$ | 423 (S) 589, 610 (Q) | 1160 | 1450 | 688 |

These peak maxima are in agreement with the spectroscopic properties of the corresponding molecular corrole (Table 6). The Soret band splitting for 1-$TiO_2$ is similar to the splitting observed for its amphiphilic molecular counterpart 2,17-bissulfonato-5,10,15-tris(pentafluorophenyl) corrole in an aqueous solution at physiologic pH, supporting the presence of the sulfonate linkage on the corrole anchored to $TiO_2$ surfaces. The splitting pattern, however, was not observed for the metalloconjugates 1-Al—$TiO_2$ and 1-Ga—$TiO_2$, owning to the presence of metal bound to deprotonated nitrogen atoms.

Figure 10:
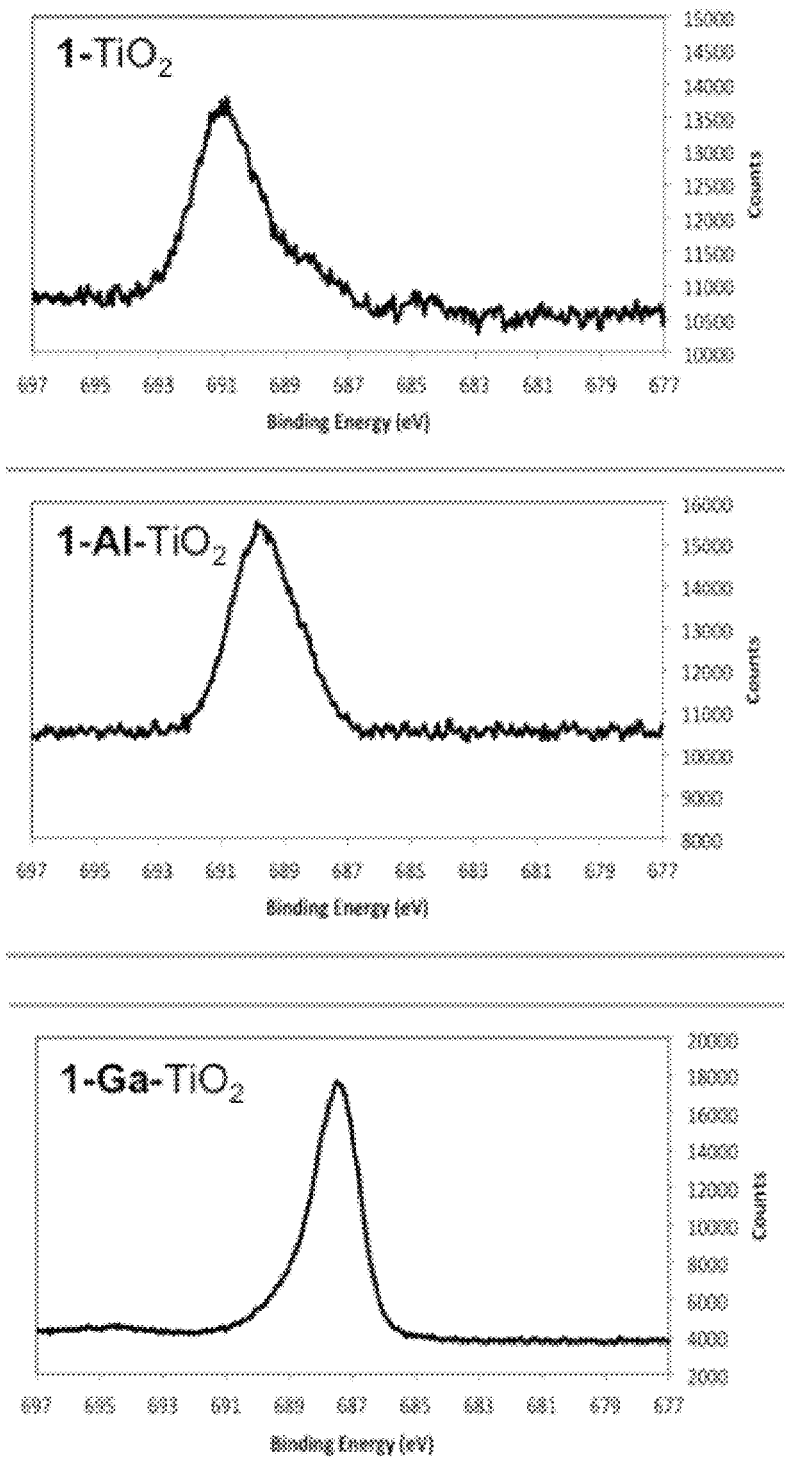
FIG. 10 depicts X-ray photoelectron spectra for nanoconjugates 1-TiO$_2$, 1-Al—TiO$_2$, and 1-Ga—TiO$_2$ exhibiting the F(1s) band.

Characterization of the fine green powder of 1-$TiO_2$, 1-Al—$TiO_2$, and 1-Ga—$TiO_2$ with FT-IR spectroscopy reveals vibrational absorption bands around 1180-1250 $cm^{-1}$ assigned to the symmetric stretching of $SO_2$ groups as well as those around 1400-1450 $cm^{-1}$ assigned to asymmetric stretching of $SO_2$ groups of covalent sulfonates. The presence of these vibrational signatures suggests that the corroles are covalently attached to the surface of $TiO_2$ through a sulfonate linkage. The vibrational frequencies for these $TiO_2$-corrole nanoconjugates are listed in Table 5. X-ray photoelectron spectroscopy was performed to study the elemental presence of the surface of the nanoparticle conjugates (Table 7). High-resolution scans for the spectra of the conjugates revealed F(1s) binding energy peaks between 688 and 691 eV, suggesting the presence of corresponding pentafluorophenyl corroles attached to the $TiO_2$ surface. See FIG. 10.

Confocal fluorescence microscopy images of aggregates of the nanoconjugates 1-$TiO_2$, 1-Al—$TiO_2$, and 1-Ga—$TiO_2$ in the solid state (FIG. 1) were taken with the samples illuminated at $\lambda_{ex}$=405 nm and the $\lambda_{em}$ recorded from 508 to 722 nm. The images for 1-Al—$TiO_2$ and 1-Ga—$TiO_2$ (FIGS. 1e and 1h) exhibit fluorescence areas on the nanoparticles compared to the relatively darker image for 1-$TiO_2$. The fluorescence signals observed with various intensities across the $TiO_2$ samples for 1-Al—$TiO_2$ and 1-Ga—$TiO_2$ also suggest that the $TiO_2$ surfaces are not evenly functionalized because of material aggregation. Selected fluorescence areas (white circles) on all three images, spectral profiles representing the nanoconjugates 1-$TiO_2$, 1-Al—$TiO_2$, and 1-Ga—$TiO_2$ were obtained (FIGS. 1c, 1f, and 1i). These spectral profiles and fluorescence signal intensities are in agreement with the fluorescence spectra (FIGS. 1a, 1d, and 1g) obtained from the molecular corroles 1, 1-Al, and 1-Ga.

Figure 2:
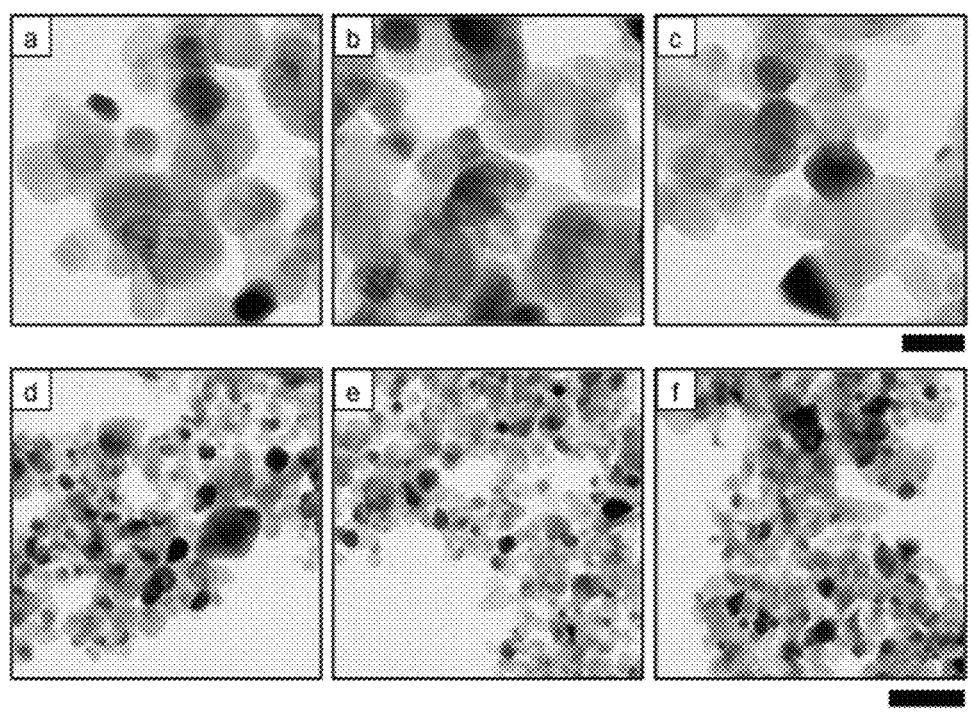
FIG. 2 depicts transmission electron microscopic (TEM) images of $TiO_2$ nanoparticles of the invention before and after dye-functionalization. (a and d) Images of the initial $TiO_2$ nanoparticles. (b and e) Images of the nanoparticles after peroxide-etching. (c and f) Images of the nanoparticles after dye functionalization. The scale bar is 25 nm for the top row and 100 nm for the bottom row of images.

The nanoconjugate 1-Al—$TiO_2$ was chosen as a candidate for cellular uptake and cytotoxic effect studies. The TEM images of $TiO_2$ (FIG. 2) show the average particle size to be 29 nm, post-corrole functionalization, albeit, they appear to aggregate. Images were taken for both before and after surface functionalization as well as for both before and after $H_2O_2$-etching. Absorption measurements of the particles embedded in a transparent polymer matrix, facilitated with the use of an integrating sphere, indicate nearly identical absorption features in the molecular and conjugated species. These experiments afforded an approximate loading of 1-Al on the surfaces of ca. 10-40 mg/g $TiO_2$. (FIG. 2).

Figure 4:
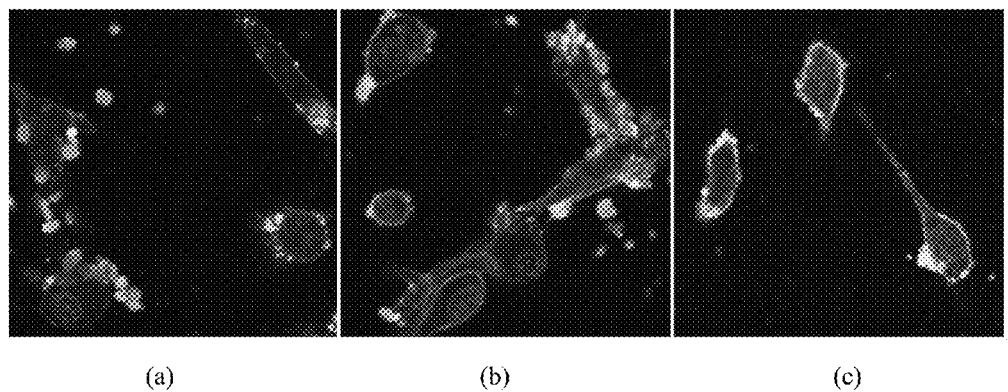
FIG. 4 depicts confocal fluorescence microscopic images of U87-Luc cells treated with 0.2 μg/mL of a preferred embodiment of the invention ($1\text{-}Al\text{-}TiO_2$) after 24 h (a), 48 h (b), and 72 h (c).

Treatment of the luciferase-transfected glioblastoma cell U87-Luc with a wide range of 1-Al—$TiO_2$ concentrations (2 ng/mL to 2 mg/mL) reveals internalization of these nanocojugates over a period of 24, 48, and 72 h as shown by the confocal fluorescence microscopic (CFM) images (FIG. 4).

The CFM images were taken after the cells were stained with the nuclear and cell membrane dyes, and washed with the media solution several times to remove the excess dyes and 1-Al—TiO2 nanoconjugates. The nucleus labeled with a Hoechst stain is seen in bluish purple ($\lambda$ex=405 nm, $\lambda$em=460 nm). The membrane seen in green is labeled with the dye FM® 1-43FX ($\lambda$ex=488 nm, $\lambda$em=580 nm). The nanoconjugate 1-Al—TiO$_2$ is observed in red ($\lambda$ex=405 nm, $\lambda$em=634 nm).

Figure 5:
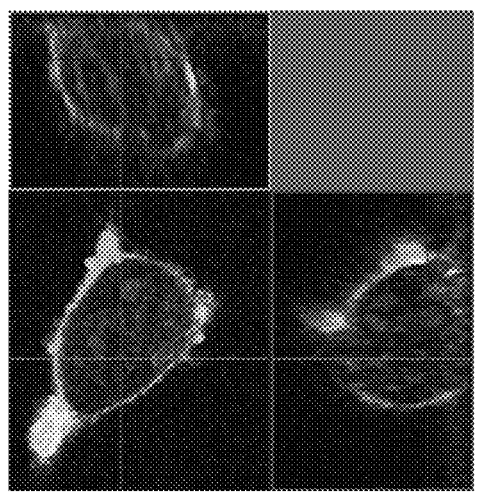
FIG. 5 depicts Z-stacked confocal fluorescence micrographic images of individual U87-Luc cells taken at 0.5-μm slice intervals after (a) 48 h and (b) 72 h of treatment with 0.2 μg/mL of a preferred embodiment of the invention ($1\text{-}Al\text{-}TiO_2$).
Figure 5:
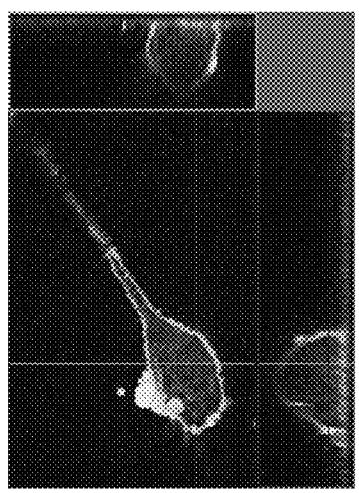

The Z-stacked confocal fluorescence microscopic (CFM) images (FIG. 5) of U87-Luc cells treated with similar concentrations (2 ng/mL to 2 mg/mL) of 1-Al—TiO$_2$ for 48 and 72 h from three different perspectives are also shown (FIG. 5). The Z-stacked CFM images of individual cells were taken at 0.5-μm slice intervals from top to bottom.

The 1-Al—TiO$_2$ nanoconstruct could also be internalized through endocytosis. Based on the confocal fluorescence images, the nanomaterials 1-Al-modified TiO$_2$ is suspended in the cytosol as opposed to the modified TiO$_2$ labeled with alizarin red S, which showed perinuclear localization in HeLa cells. These findings suggest a distribution pattern of the TiO$_2$ nanoconjugates within the cells similar to another study, in which 1-D TiO$_2$ nanorods and nanoparticles labeled with fluorescein thiocyanate were internalized into HeLa cells after a given period of time. The internalization of 1-Al—TiO$_2$ into glioblastoma cells can also be observed even at a very low concentration range (<μg/mL).

Figure 6:
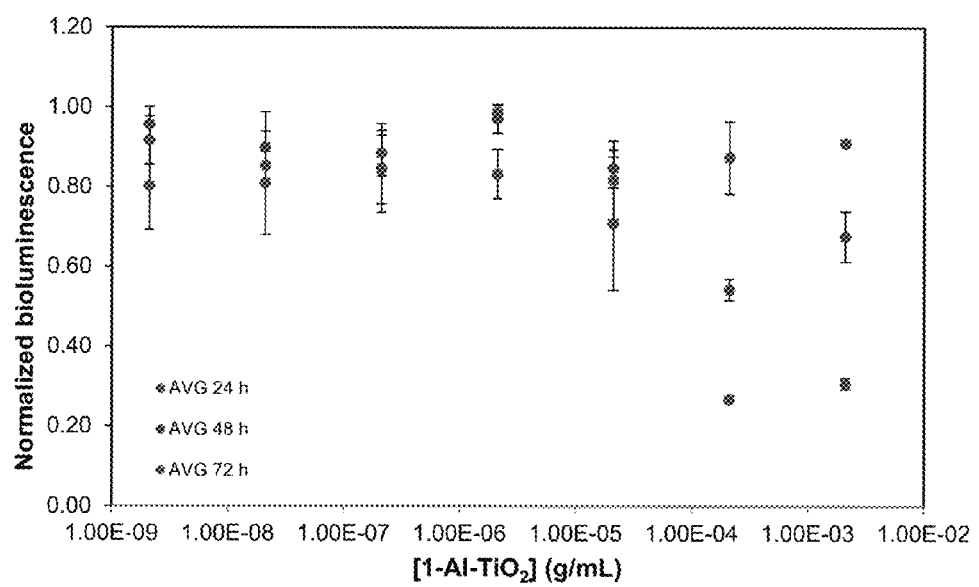
FIG. 6 depicts a cell viability plot of U87-Luc cells treated by of a preferred embodiment of the invention ($1\text{-}Al\text{-}TiO_2$) at various concentrations (2 ng/mL to 2 mg/mL) using a bioluminescence assay.

TiO$_2$ nanoparticles exhibit various degrees of cytotoxic activities upon photoactivation by UV-Vis light leading to formation of reactive oxygen species. To best study and understand the cytotoxic effect of the 1-Al—TiO$_2$ conjugate that is not related to the photocatalytic property of TiO$_2$ on cell death, the glioblastoma cell U87-Luc was treated in the absence of UV-Vis irradiation with the same range of 1-Al—TiO$_2$ concentrations (2 ng/mL to 2 mg/mL) as in the cell internalization studies. The cells were incubated over a period of 24, 48, and 72 h prior to bioluminescence cell viability assays. Based on the bioluminescence signal of the firefly luciferin from living U87-Luc cells, which is related to the level of cellular ATP, the cytotoxic assay shows that the nanoconjugate 1-Al—TiO$_2$ has essentially no cytotoxic effect on the glioblastoma cells after 24 h of treatment (FIG. 6) and, therefore, could be considered biocompatible. On the other hand, the cytotoxic effect becomes more apparent as the cells were exposed to the corrole-TiO$_2$ nanoparticles for extended periods of time at higher concentrations (>200 μg/mL). For example, only ca. 65% and ca. 30% of the bioluminescence signals from the live cells were observed after the 48-h and 72-h treatments at 2 mg/mL, respectively. This viability study of the U87-Luc cells treated with 1-Al—TiO$_2$ is also consistent with a study performed on mouse fibroblast cells, using the MTT assay, showing that the cytotoxic effects of TiO$_2$ at various concentrations (3 to 600 μg/mL) were negligible after 24 h of treatment whereas the 48-h treatment of these cells with the nanoparticle showed decrease in cell viability at higher concentrations. Another study on the cytotoxicity effect of unmodified 1-D and 3-D TiO$_2$ on HeLa cell also show that these nanoparticles were relatively nontoxic at concentrations up to 125 μg/mL in the absence of light.

Figure 7:
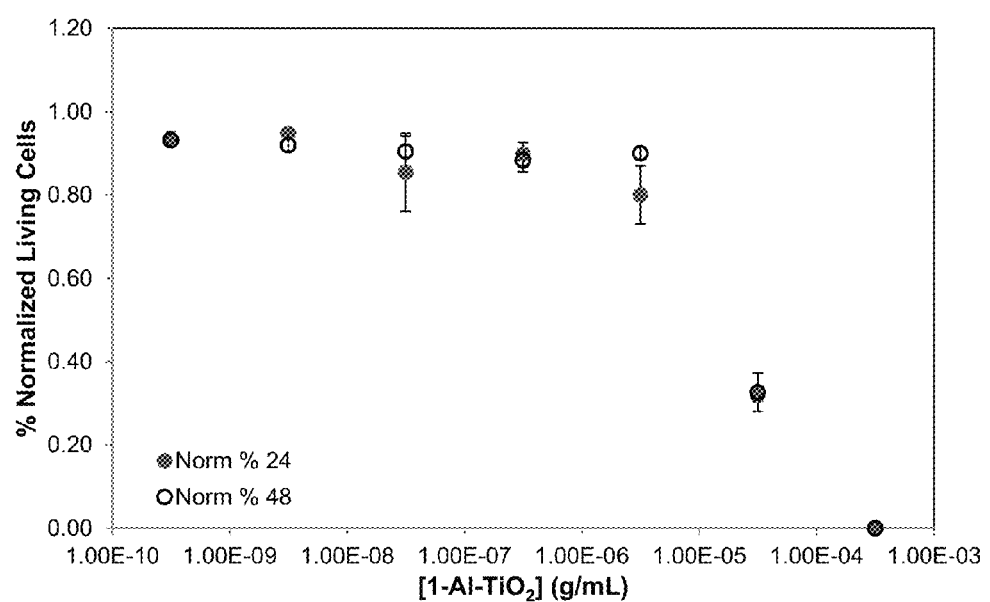
FIG. 7 depicts the results of mouse primary hepatocytes (MPH) treated with a preferred embodiment of the invention ($1\text{-}Al\text{-}TiO_2$) in various concentrations (0.3 ng/mL to 0.3 mg/mL) for 24 and 48 h.

Additionally, to compare the cytotoxic effect of the nanoconjugate 1-Al—TiO$_2$ on cancer and normal cells, mouse primary hepatocytes (MPH) were treated with 1-Al—TiO$_2$ in various concentrations (0.3 ng/mL to 0.3 mg/mL) for 24 and 48 h (FIG. 7). It was observed that 1-Al—TiO$_2$ was also essentially nontoxic up to 3 μg/mL after both 24 and 48 h of treatment. Only at higher concentrations were the ratios of the live cells dropped below 80%. The MPH behave similarly after 24-h and 48-h treatments with various doses of 1-Al—TiO$_2$, suggesting that low 1-Al—TiO$_2$ concentrations have minimal cytotoxic effects on the viability of these normal cells. While the trend at high concentrations were not observed for the glioblastoma U870-Luc cells treated with 1-Al—TiO$_2$, it is expected that normal cells, especially primary cells, are less tolerant towards exogenous non-native agents. Nonetheless, the intense fluorescence exhibited by 1-Al would allow for the use of the nanoconjugate 1-Al—TiO$_2$ as an optical imaging agent observable by confocal fluorescence microscopy even at low concentrations (20-200 ng/mL) below the cytotoxic thresholds for both the cancer and normal cells observed in the studies.

4-(chlorosulfonyl)Benzoic Acid+TiO$_2$ (Anatase)

Added TiO$_2$ (0.1099 g) and 4-(chlorosulfonyl)Benzoic Acid (0.0171 g) to scintillation vial. Pumped into dry box. Added anhydrous Pyridine (3 mL) and heated to 120° C. for 1 hr, under an inert atmosphere. Allowed to cool to room temperature, then added 2 mL H$_2$O, which then centrifuged down. Washed and centrifuged with acetone, acetone, water, and acetone. Pumped down on high vacuum line to afford product for Infrared Spectroscopy.

Biphenyl-4-sulfonyl Chloride+TiO$_2$ (Anatase)

Added TiO$_2$ (0.1253 g) and Biphenyl-4-sulfonyl Chloride (0.0208 g) to scintillation vial. Pumped into dry box. Added anhydrous Pyridine (3 mL) and heated to 120° C. for 1 hr, under an inert atmosphere. Allowed to cool to room temperature, then added 2 mL H$_2$O, which then centrifuged down. Washed and centrifuged with acetone, acetone, water, and acetone. Pumped down on high vacuum line to afford product for Infrared Spectroscopy.

4'-chlorobiphenyl-4-sulfonyl Chloride+TiO$_2$ (Anatase)

Added TiO$_2$ (0.1205 g) and 4'-chlorobiphenyl-4-sulfonyl Chloride (0.0210 g) to scintillation vial. Pumped into dry box. Added anhydrous Pyridine (3 mL) and heated to 120° C. for 1 hr, under an inert atmosphere. Allowed to cool to room temperature, then added 2 mL H$_2$O, which then centrifuged down. Washed and centrifuged with acetone, acetone, water, and acetone. Pumped down on high vacuum line to afford product for Infrared Spectroscopy.

Chlorsulfonyl Isocyante+TiO$_2$ (Anatase)

Added TiO$_2$ (0.1205 g) to scintillation vial. Pumped into dry box. Added 100 μL Chlorsulfonyl Isocyante. Added anhydrous Pyridine (3 mL) and heated to 120° C. for 1 hr, under an inert atmosphere. Allowed to cool to room temperature, then added 2 mL H$_2$O, which then centrifuged down. Washed and centrifuged with acetone, acetone, water, and acetone. Pumped down on high vacuum line to afford product for Infrared Spectroscopy.

Chlorsulfonyl Isocyante+TiO$_2$ (Anatase)

Added TiO$_2$ (0.1269 g) to scintillation vial. Pumped into dry box. Added 400 μL Chlorsulfonyl Isocyante. Heated to 120° C. for 1 hr, under an inert atmosphere. Allowed to cool to room temperature, then added 4 mL H$_2$O, which was then centrifuged down. Washed and centrifuged with acetone, acetone, water, and acetone. Pumped down on high vacuum line to afford product for Infrared Spectroscopy.

According to the methods described herein, other Cl-SO$_2$-containing substrates can also be employed, such as, for example, 2-pentyl sulfonyl chloride, 3,3,3-trifluoropropane-1-sulfonyl chloride, methyl(chlorosulfonyl)acetate, and the like.

A)

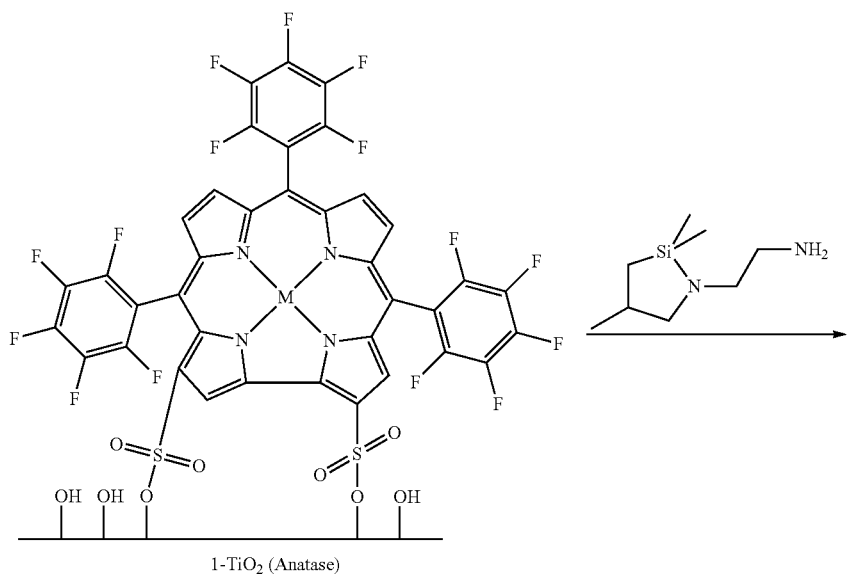

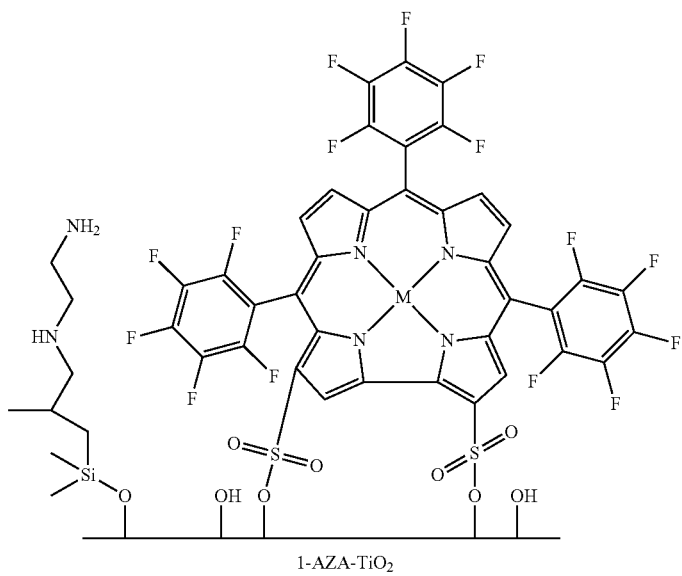

Step 1: 1-TiO₂ (Anatase) (163.3 mg) and a stir bar were pumped overnight under high vacuum in an 8 mL scintillation vial.

Step 2: The reaction mixture was returned to an argon atmosphere, to which was added anhydrous toluene (5 mL). The reaction was stirred and then dispersed using a sonicator. The reaction was placed under an inert atmosphere again using a needle and schlenck line. To the reaction mixture was added N-aminoethyl-aza-2,2,4-trimethylsilacyclopentane (0.4 mL) (Gelest). The reaction was then vented thoroughly with an argon atmosphere and vent needle. Left to stir, sealed under Ar, at RT for 24 hours.

Alternative: 1-TiO₂ (163.3 mg) were pumped overnight at high vacuum, and then returned to an argon atmosphere. To this reaction was added anhydrous toluene (5 mL), and the suspension was dispersed using a sonicating bath. To this suspension was then added N-aminoethyl-aza-2,2,4-trimethylsilacyclopentane (.4 mL). The reaction mixture was dispersed again using a sonicating bath and then sealed under an argon atmosphere. The reaction was set to stir at room temperature for 26 hours in the absence of light. After 26 hours, the reaction was vented to air and diluted with acetone. The reaction was then centrifuged and washed.

Step 3: The reaction mixture was vented the reaction to air, diluted with acetone and then centrifuged (2 minutes at 3500 rcf). Washed and centrifuged with acetone, dichloromethane, and acetone (2 minutes at 3500 rcf). Washed and centrifuged with water (4 min at 5000 rcf). Pumped down on high vacuum overnight to afford 1-AZA-TiO$_2$ (.1270 g).

B)

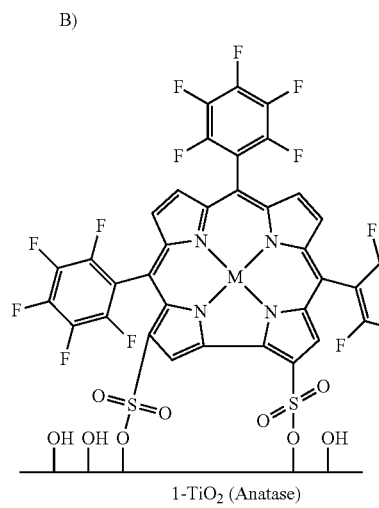

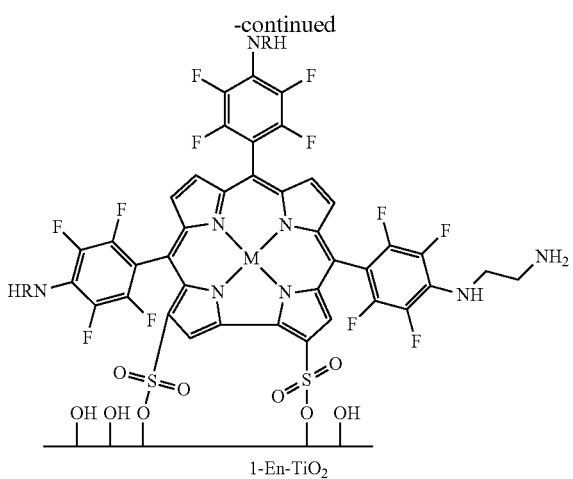

Step 1: 1-TiO$_2$ (Anatase) (163.3 mg) and a stir bar were pumped overnight under high vacuum in an 8 mL scintillation vial.

Step 2: Under inert atmosphere, ethylenediamine (5 mL, non-distilled) was added. The reaction was stirred and then dispersed using a sonicator. The reaction was then vented thoroughly with an argon atmosphere and vent needle. Left to stir, sealed under Ar, at 115° C. for 24 hours.

Step 3: Vented the reaction to air and diluted with acetone and then centrifuged (2 minutes at 3500 rcf). Washed and centrifuged with acetone, dcm, and acetone (2 minutes at 3500 rcf). Washed and centrifuged with water (4 min at 5000 rcf). Pumped down on high vacuum overnight to afford 1-En-TiO$_2$(.1176 g).

C)

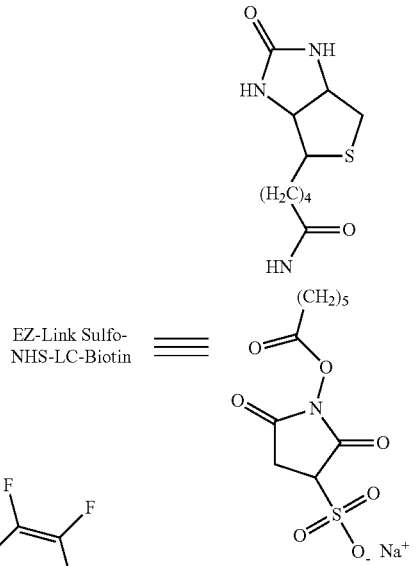

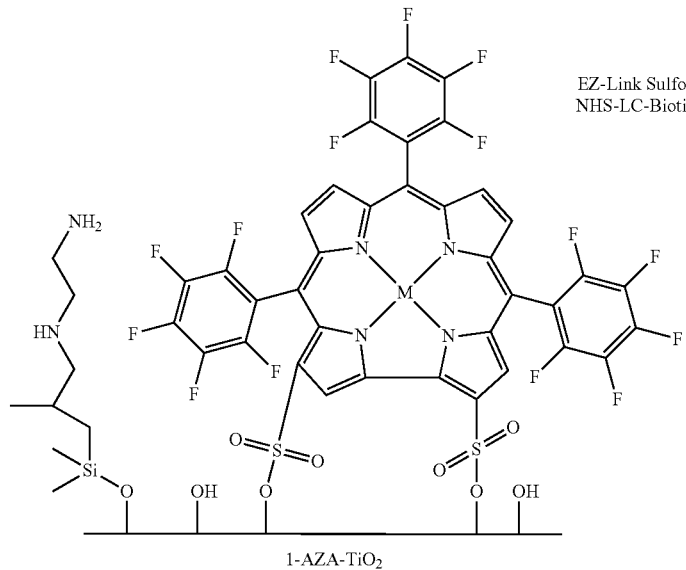

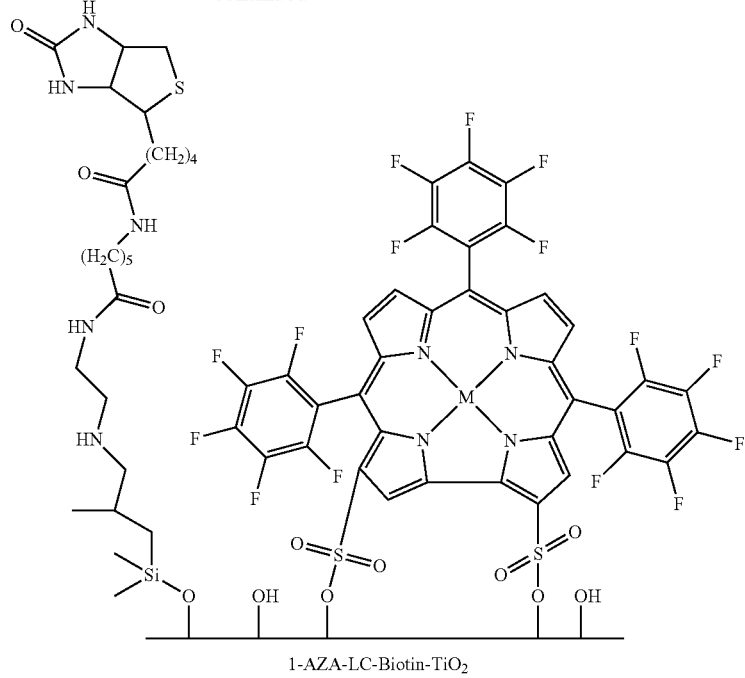

1-AZA-LC-Biotin-TiO₂

Step 1: Added 1-AZA-TiO₂ (0.0550 g) and EZ-Link Sulfo-NHS-LC-Biotin (0.0139 g) to an 8 mL scintillation vial, with a stir bar. Then added PBS (4 mL). The reaction was dispersed with a sonnicator and then set to stir. The reaction was diluted (to 9.5 mL). The reaction was then centrifuged and washed three times (3 min/5000 rcf) with water. The reaction was suspended in water then transferred to an empty 8 mL scintillation vial and frozen in liquid nitrogen. The sample was placed in a vacuum chamber for lyophilization.

Step 2: The lyophilized solid was isolated to afford 1-AZA-LC-Biotin-TiO₂ (0.0472 g).

D)

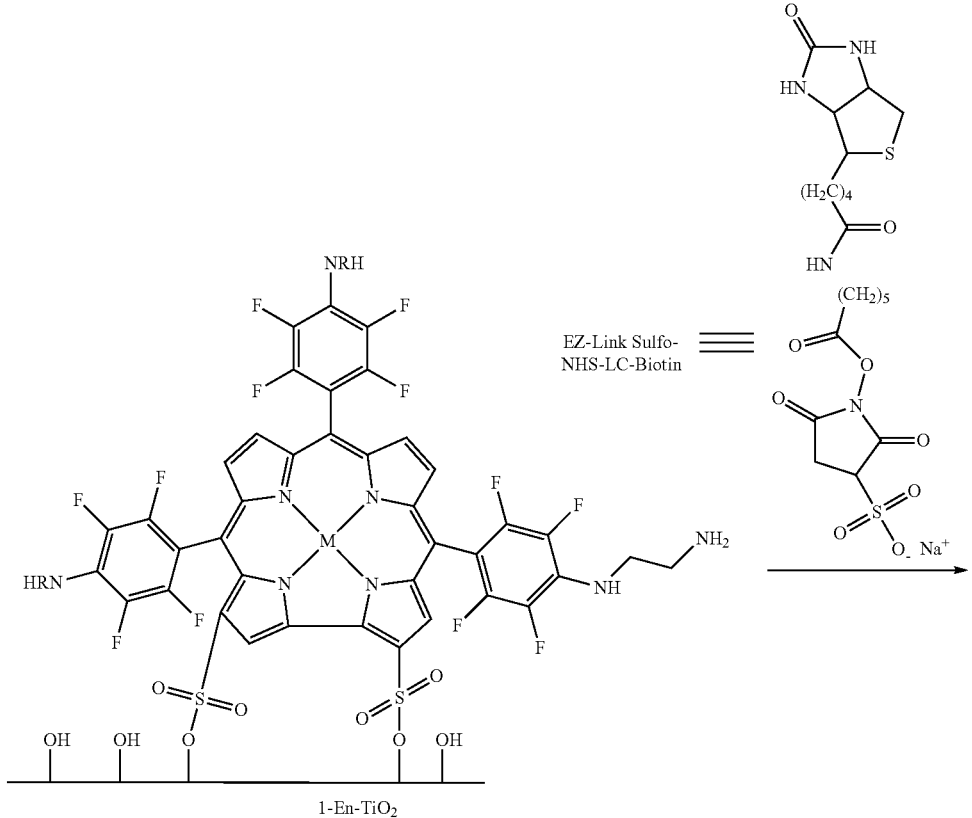

-continued

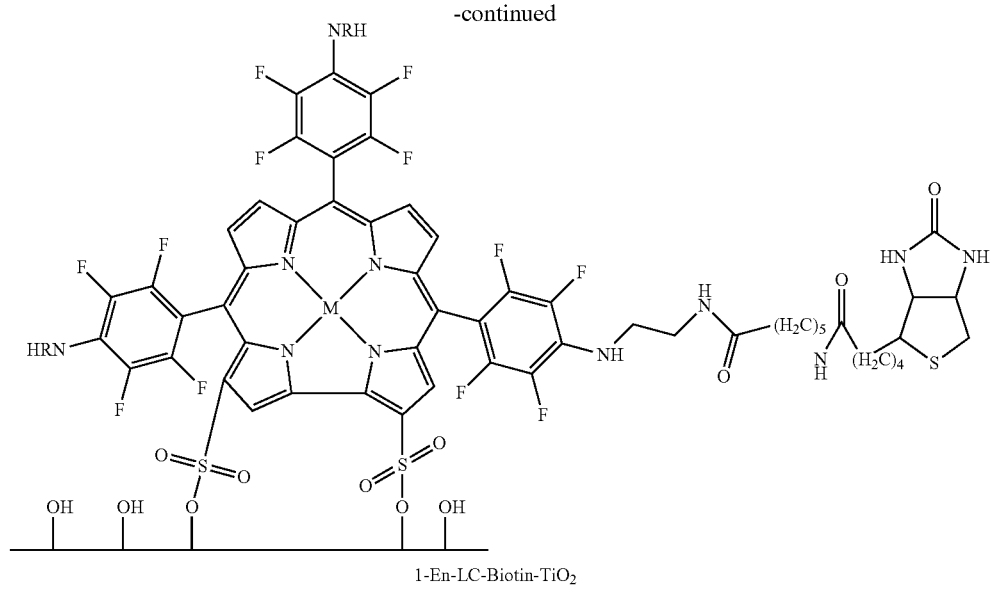

1-En-LC-Biotin-TiO₂

Step 1: Added 1-EN-TiO₂ (0.0551 g) and EZ-Link Sulfo-NHS-LC-Biotin (.0146 g) to an 8 mL scintillation vial, with a stir bar. Then added PBS (4 mL). The reaction was dispersed with a sonnicator and then set to stir. The reaction was diluted (to 9.5 mL). The reaction was then centrifuged and washed three times (3 min/5000 rcf) with water. The reaction was suspended in water then transferred to an empty 8 mL scintillation vial and frozen in liquid nitrogen. The sample was placed in a vacuum chamber for lyophilization.

Step 2: The lyophilized solid was isolated to afford 1-AZA-LC-Biotin-TiO₂ (0.0434 g).

What is claimed:

1. A material according to formula I:

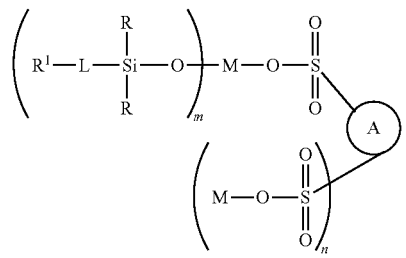

I wherein A is a corrolyl or metallated corrolyl;
M is a surface comprising $TiO_2$, $BaTiO_3$, $SnO_2$, $Al_2O_3$, $Fe_2O_3$, $Fe_3O_4$, $ZrO_2$, $CeO_2$, $CdO$, $Cr_2O_3$, $CuO$, $MnO$, $Mn_2O_3$, $MnO_2$, $NiO$, $SnO$, $SnO_2$, $SiO_2$, or $ZnO$;
each R is independently $C_{1-6}$alkyl;
L is a linker;
each $R^1$ is a non-antibody moiety or an antibody moiety, wherein the non-antibody moiety or the antibody moiety is optionally complexed to a target;
m is 1, 2, 3, or 4; and
n is 0 or 1.

2. The material according to claim 1, wherein the surface is a nanoparticle surface.

3. The material according to claim 1, wherein the corrolyl is:

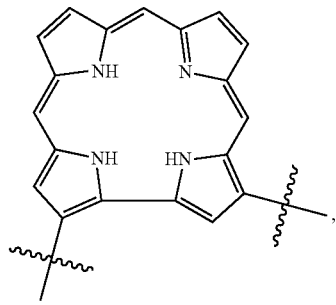

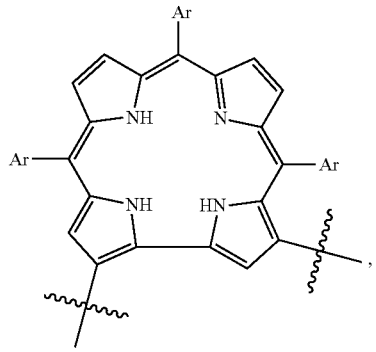

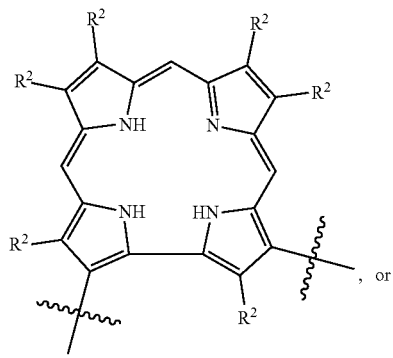

, or

-continued

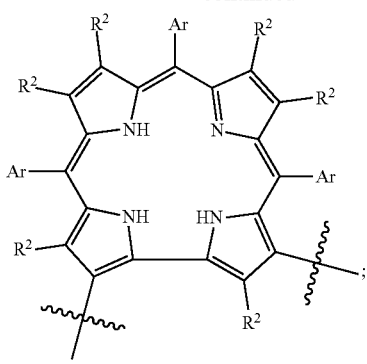

wherein

Ar is phenyl or naphthyl, wherein the phenyl or naphthyl is optionally substituted with one or more substituents independently selected from the group consisting of halogen and —$NR^3R^4$, wherein $R^3$ and $R^4$ are each independently H, $C_{1-10}$ alkyl, $C_{1-10}$alkenyl, or -alkaryl; or $R^3$ and $R^4$, together with the nitrogen atom to which they are attached, form a heterocycloalkyl ring that is optionally substituted with $C_{1-6}$alkyl; and each $R^2$ is independently H, $C_{1-6}$alkyl, halogen, or M-O—$SO_2$—.

4. The material according to claim 1, wherein the corrolyl is:

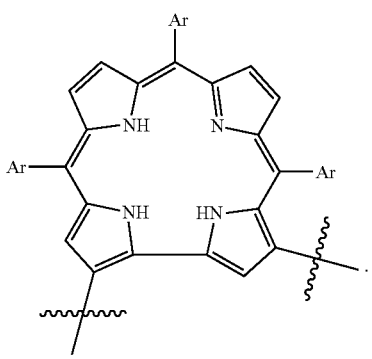

5. The material according to claim 4, wherein each Ar is pentafluorophenyl.

6. The material according to claim 1, wherein the metallated corrolyl is:

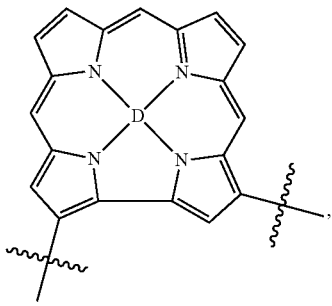

-continued

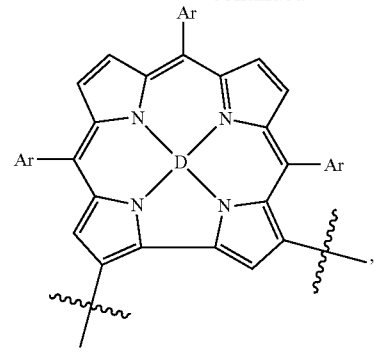

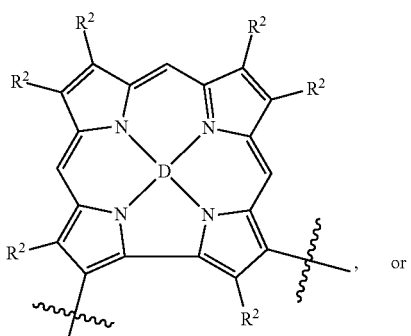, or

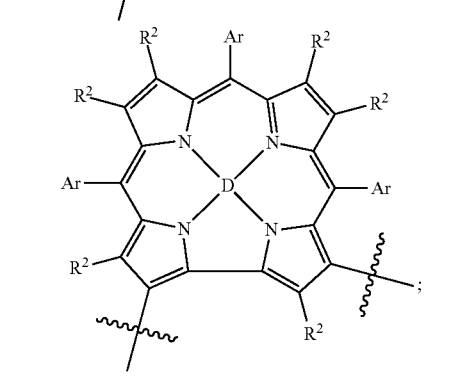;

wherein

D is Al, Ga, Fe, Mn, Sb, Co, Cr, Rh, Ru, Ro, Ir, V, Re, Cu, Sn, Ge, Ti, or Mo, each of which is optionally coordinated to one or more ligands.

7. The material according to claim 6, wherein D is Al or Ga.

8. The material according to claim 6, wherein the metallated corrolyl is

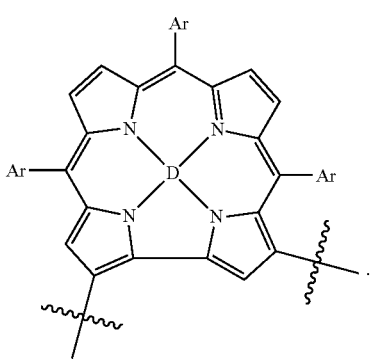

9. The material according to claim 8, wherein each Ar is pentafluorophenyl.

10. The material according to claim 9 wherein D is Al(ligand)$_2$ or Ga(ligand).

11. The material according to claim 10, wherein the ligand is pyridine.

12. The material according to claim 1, wherein n is 0.

13. The material according to claim 1, wherein n is 1.

14. The material according to claim 1, wherein m is 1.

15. The material according to claim 1, wherein m is 2.

16. The material according to claim 1, wherein m is 3.

17. The material according to claim 1, wherein m is 4.

18. The material according to claim 1, wherein each R is methyl.

19. The material according to claim 1, wherein L is

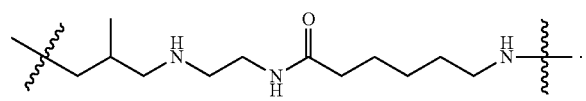 [SMILES: *CC(C)CNCCNC(=O)CCCCCN*]

20. The material according to claim 1, wherein R$^1$ is a non-antibody moiety selected from the group consisting of a biotin moiety, an Arg-Gly-Asp moiety, an Asn-Gly-Arg moiety, a folate moiety, a transferrin moiety, a granulocyte-macrophage colony-stimulating gactor moiety, a galactosamine moiety, a hyaluronic acid moiety, a HERPBK10 moiety, and an F3 moiety.

21. The material according to claim 1, wherein R$^1$ is an antibody moiety selected from the group consisting of an anti-VEGFR antibody, an anti-ERBB2 moiety, an anti-CD19 moiety, an anti-CD20 moiety, an anti-CD22 moiety, an anti-CD25 moiety, an anti-CD33 moiety, an anti-HLA-CD10b moiety, an anti-tenascin moiety, an anti-CEA moiety, an anti-MUC1 moiety, and an anti-TAG72 moiety.

22. The material according to claim 1, wherein the non-antibody moiety or antibody moiety is complexed to a target.

23. The material according to claim 1 that is:

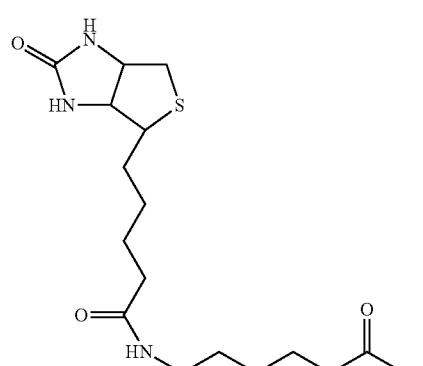

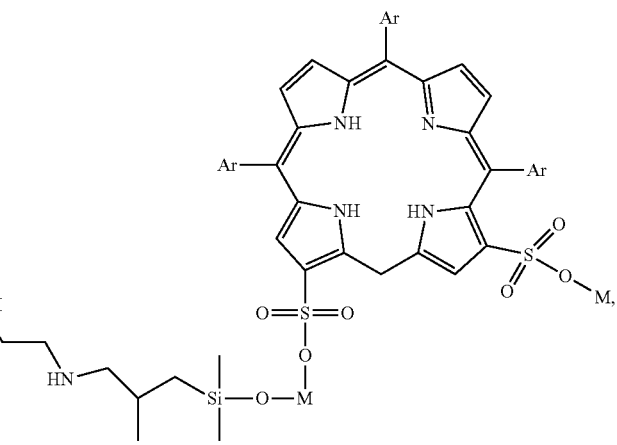

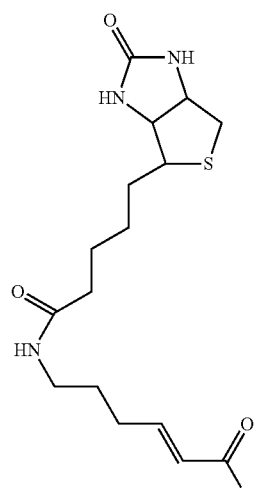

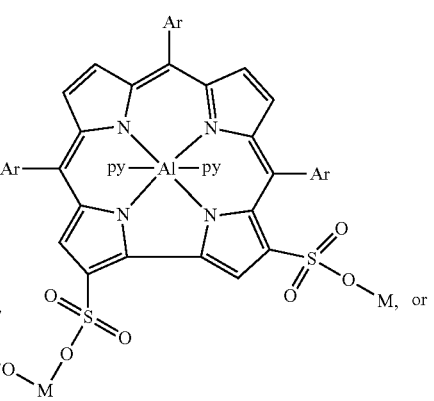

-continued

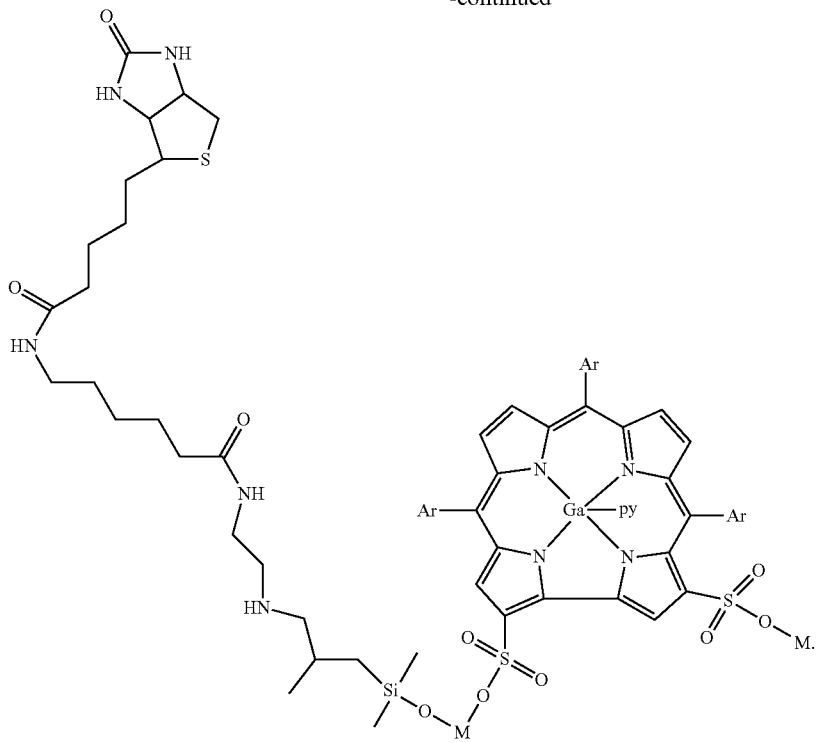

24. The material according to claim 23, wherein each Ar is pentafluorophenyl.

25. The material according to claim 23, wherein M is TiO$_2$.

26. A material according to formula II

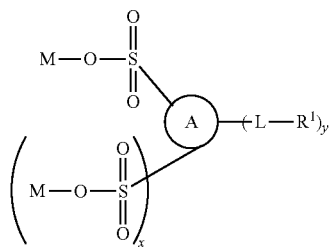

wherein A is a corrolyl or metallated corrolyl;
M is a surface comprising TiO$_2$, BaTiO$_3$, SnO$_2$, Al$_2$O$_3$, Fe$_2$O$_3$, Fe$_3$O$_4$, ZrO$_2$, CeO$_2$, CdO, Cr$_2$O$_3$, CuO, MnO, Mn$_2$O$_3$, MnO$_2$, NiO, SnO, SnO$_2$, SiO$_2$, or ZnO;
L is a linker;
R$^1$ is a non-antibody moiety or an antibody moiety, wherein the non-antibody moiety or the antibody moiety is optionally complexed to a target;
y is 1, 2, or 3; and
x is 0 or 1.

27. The material according to claim 26, wherein the surface is a nanoparticle surface.

28. The material according to claim 26, wherein the corrolyl is:

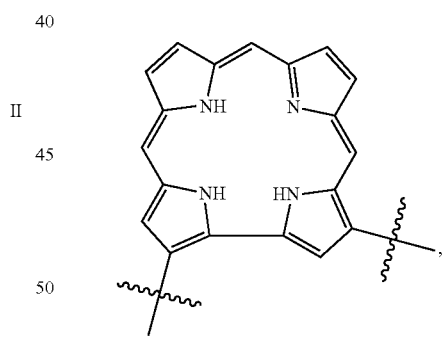

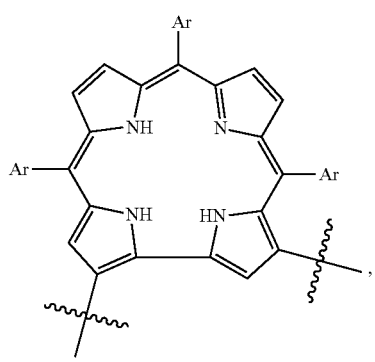

-continued

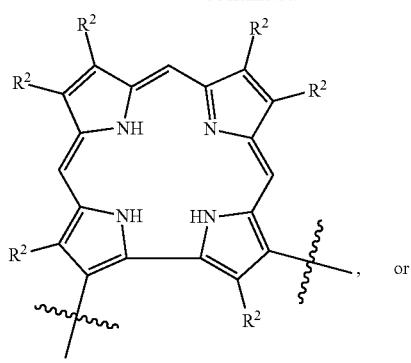, or

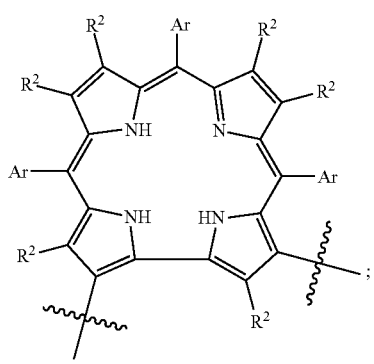;

wherein

Ar is phenyl or naphthyl, wherein the phenyl or naphthyl is optionally substituted with one or more substituents independently selected from the group consisting of halogen and —NR$^3$R$^4$, wherein R$^3$ and R$^4$ are each independently H, C$_{1-10}$alkyl, C$_{1-10}$alkenyl, or -alkaryl; or R$^3$ and R$^4$, together with the nitrogen atom to which they are attached, form a heterocycloalkyl ring that is optionally substituted with C$_{1-6}$alkyl; and each R$^2$ is independently H, C$_{1-6}$alkyl, halogen, or M-O—SO$_2$—.

29. The material according to claim 26, wherein the corrolyl is:

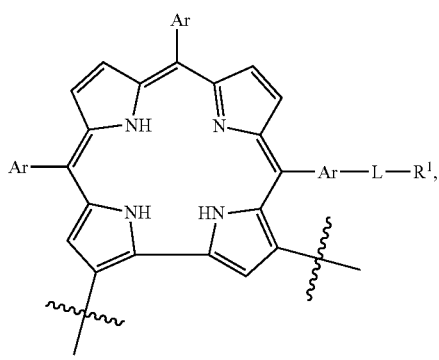

-continued

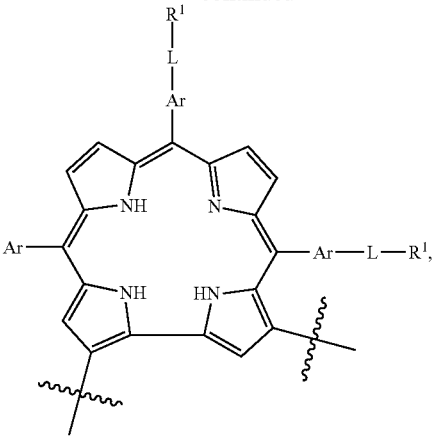

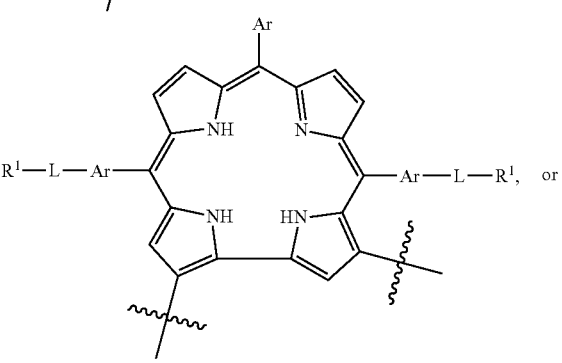, or

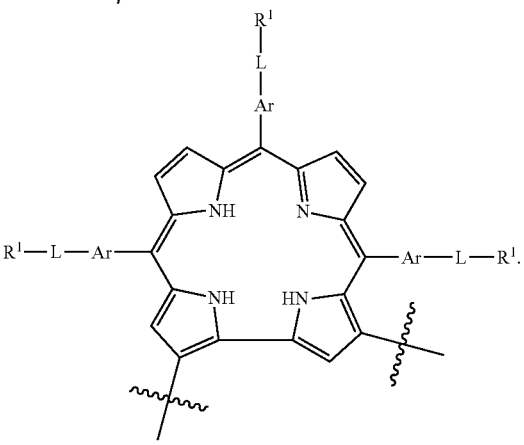.

30. The material according to claim 26, wherein the metallated corrolyl is:

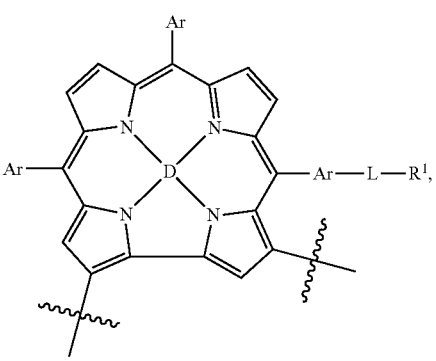

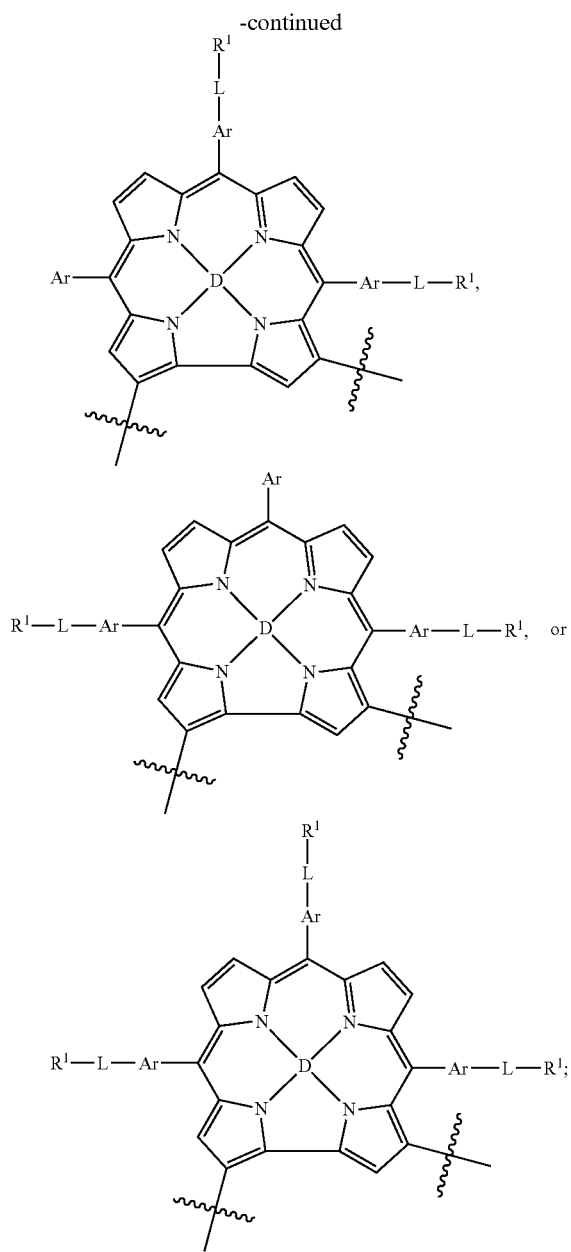

wherein

D is Al, Ga, Fe, Mn, Sb, Co, Cr, Rh, Ru, Ro, Ir, V, Re, Cu, Sn, Ge, Ti, or Mo, each of which is optionally coordinated to one or more ligands.

31. The material according to claim 30, wherein D is Al or Ga.

32. The material according to claim 31 wherein D is Al(ligand)$_2$ or Ga(ligand).

33. The material according to claim 32, wherein the ligand is pyridine.

34. The material according to claim 26, wherein x is 0.

35. The material according to claim 26, wherein x is 1.

36. The material according to claim 26, wherein y is 1.

37. The material according to claim 26, wherein y is 2.

38. The material according to claim 26, wherein y is 3.

39. The material according to claim 26, wherein L is

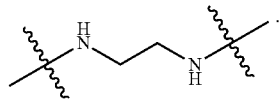

40. The material according to claim 26, wherein $R^1$ is a non-antibody moiety selected from the group consisting of a biotin moiety, an Arg-Gly-Asp moiety, an Asn-Gly-Arg moiety, a folate moiety, a transferrin moiety, a granulocyte-macrophage colony-stimulating gactor moiety, a galactosamine moiety, a hyaluronic acid moiety, a HERPBK10 moiety, and an F3 moiety.

41. The material according to claim 26, wherein $R^1$ is an antibody moiety selected from the group consisting of an anti-VEGFR antibody, an anti-ERBB2 moiety, an anti-CD19 moiety, an anti-CD20 moiety, an anti-CD22 moiety, an anti-CD25 moiety, an anti-CD33 moiety, an anti-HLA-CD10b moiety, an anti-tenascin moiety, an anti-CEA moiety, an anti-MUC1 moiety, and an anti-TAG72 moiety.

42. The material according to claim 26, wherein the non-antibody moiety or antibody moiety is complexed to a target.

43. The material according to claim 26 that is:

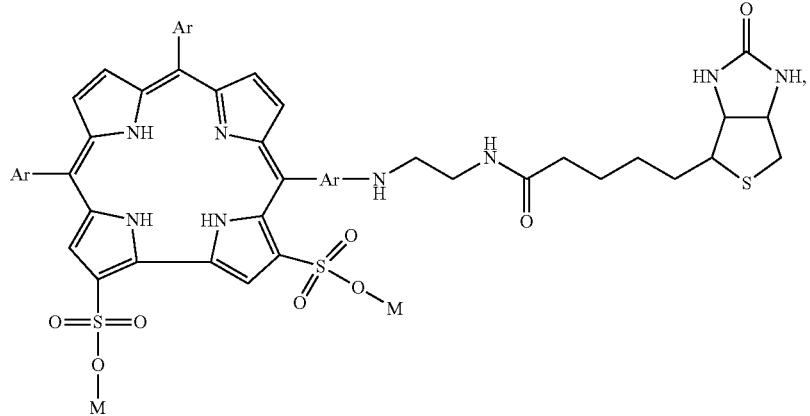

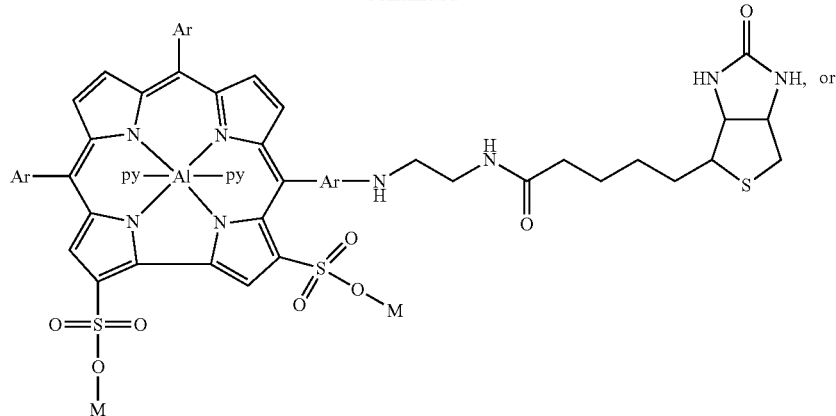
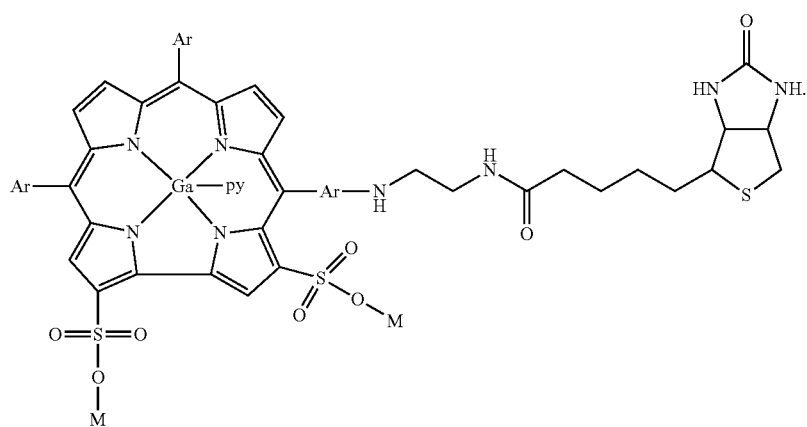
44. The material according to claim 43, that is
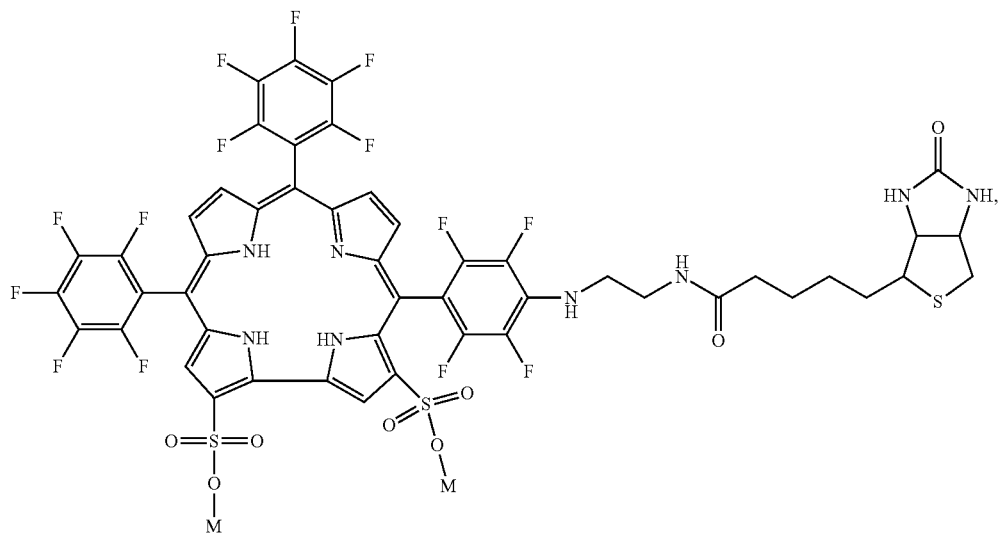

-continued

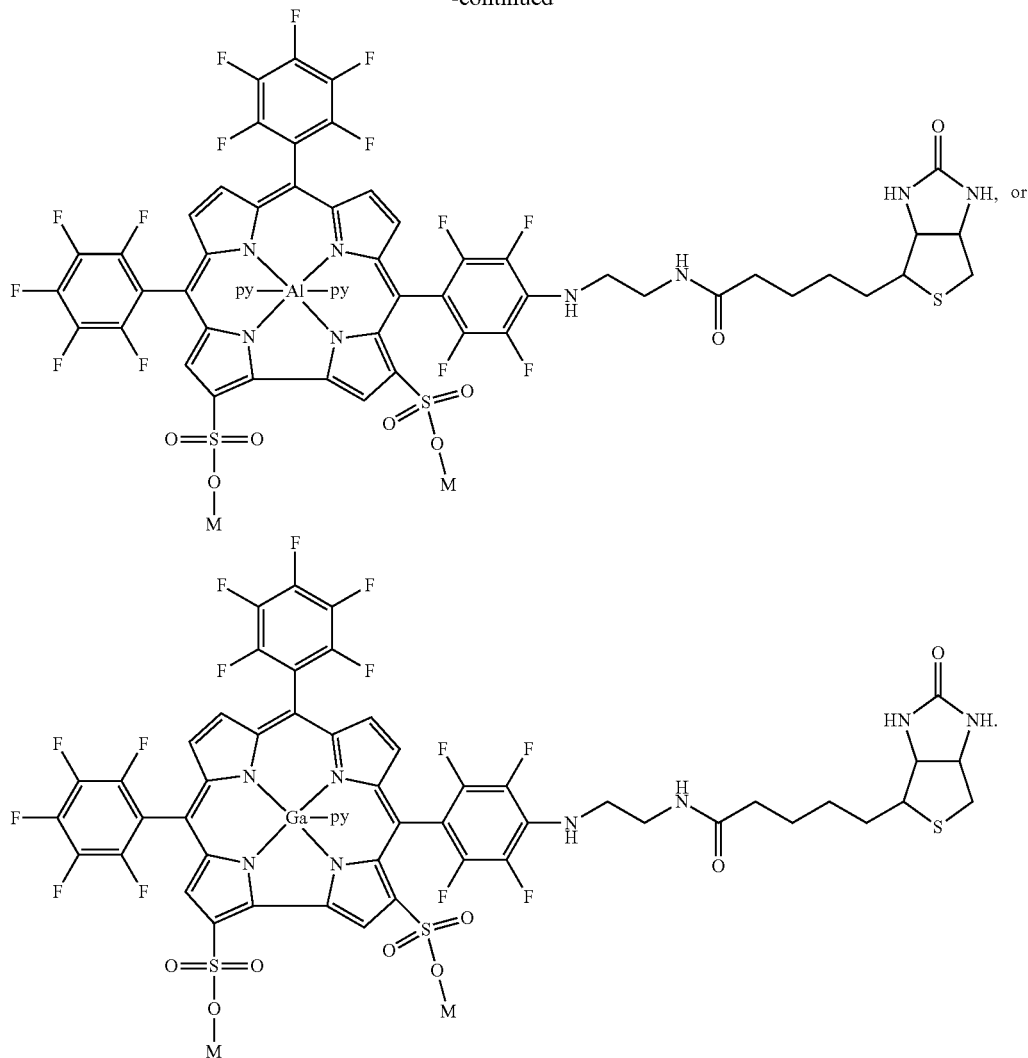

45. The material according to claim 26, wherein M is TiO₂.

46. A method of imaging a tissue in a patient comprising: administering to the patient a material according to claim 1 or claim 26, wherein A is a metallated corrolyl; and imaging the tissue using imaging.

47. The method of claim 46, wherein the imaging is optical imaging.

48. The method of claim 47, wherein the optical imaging is fluorescence imaging.

49. The method of claim 46, wherein the imaging is magnetic resonance imaging.

50. The method of claim 46, wherein the imaging is positron emission tomography.

51. The method of claim 46, wherein the tissue is bone, bone marrow, neural tissue, fibrous connective tissue, cartilage, muscle, vasculature, skin, adipose tissue, blood, or glandular tissue.

52. The method of claim 46, wherein the tissue is cancerous tissue.

* * * * *